(12) United States Patent
Cai et al.

(10) Patent No.: US 8,703,096 B2
(45) Date of Patent: Apr. 22, 2014

(54) BETA-AMYLOID PET IMAGING AGENTS

(75) Inventors: Lisheng Cai, Derwood, MD (US);
Victor W. Pike, Bethesda, MD (US);
Robert B. Innis, Rockville, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 914 days.

(21) Appl. No.: 12/293,340

(22) PCT Filed: Apr. 19, 2007

(86) PCT No.: PCT/US2007/066939
§ 371 (c)(1),
(2), (4) Date: Sep. 22, 2010

(87) PCT Pub. No.: WO2007/124345
PCT Pub. Date: Nov. 1, 2007

(65) Prior Publication Data
US 2011/0008255 A1     Jan. 13, 2011

Related U.S. Application Data

(60) Provisional application No. 60/793,807, filed on Apr. 21, 2006.

(51) Int. Cl.
| A61K 51/00 | (2006.01) |
| A61M 36/14 | (2006.01) |
| A61K 38/00 | (2006.01) |
| A61P 25/28 | (2006.01) |
| A61K 31/00 | (2006.01) |

(52) U.S. Cl.
CPC .................................... *A61K 51/00* (2013.01)
USPC ........................................ 424/1.11; 514/17.8

(58) Field of Classification Search
USPC ........................................................ 424/1.11
See application file for complete search history.

(56) References Cited

U.S. PATENT DOCUMENTS

| 4,716,169 A * | 12/1987 | Heider et al. ................. 514/299 |
| 6,858,633 B1 * | 2/2005 | Stevens et al. ................ 514/367 |
| 2008/0219922 A1 * | 9/2008 | Goodman et al. ........... 424/1.65 |

OTHER PUBLICATIONS

Cai, L., et al., "Synthesis and Evaluation of Two $^{18}$F-Labeled 6-Iodo-2-(4'-N,N-dimethylamino)phenylimidazo[1,2-a]pyridine Derivatives as Prospective Radioligands for β-Amyloid in Alzheimer's Disease," *J. Med. Chem.*, vol. 47, pp. 2208-2218 (2004).

* cited by examiner

*Primary Examiner* — Michael G Hartley
*Assistant Examiner* — Melissa Perreira
(74) *Attorney, Agent, or Firm* — Cantor Colburn LLP

(57) ABSTRACT

Novel derivatives of imidazopyridinylbenzeneamines and novel derivatives of benzothiazolylbenzeneamines are disclosed that offer improved behavior when used as imaging agents for positron emission tomography of beta-amyloids. Also disclosed is a palladium-catalyzed reaction scheme under microwave conditions for aryl thioethers in general that provides a high ratio of substitution relative to reduction and can be used for the imidazopyridinylbenzeneamine derivatives as well as other compounds of related structure.

12 Claims, 4 Drawing Sheets

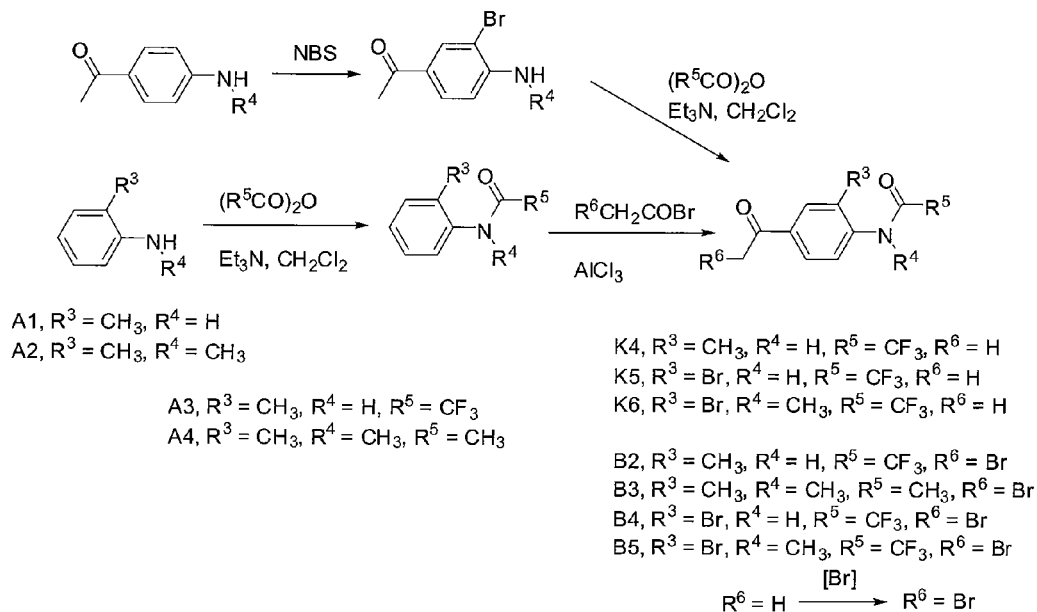

Figure 3:
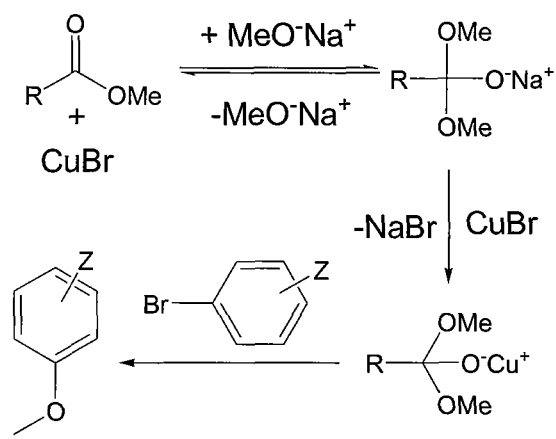

A1, $R^3$ = $CH_3$, $R^4$ = H
A2, $R^3$ = $CH_3$, $R^4$ = $CH_3$

A3, $R^3$ = $CH_3$, $R^4$ = H, $R^5$ = $CF_3$
A4, $R^3$ = $CH_3$, $R^4$ = $CH_3$, $R^5$ = $CH_3$

K4, $R^3$ = $CH_3$, $R^4$ = H, $R^5$ = $CF_3$, $R^6$ = H
K5, $R^3$ = Br, $R^4$ = H, $R^5$ = $CF_3$, $R^6$ = H
K6, $R^3$ = Br, $R^4$ = $CH_3$, $R^5$ = $CF_3$, $R^6$ = H

B2, $R^3$ = $CH_3$, $R^4$ = H, $R^5$ = $CF_3$, $R^6$ = Br
B3, $R^3$ = $CH_3$, $R^4$ = $CH_3$, $R^5$ = $CH_3$, $R^6$ = Br
B4, $R^3$ = Br, $R^4$ = H, $R^5$ = $CF_3$, $R^6$ = Br
B5, $R^3$ = Br, $R^4$ = $CH_3$, $R^5$ = $CF_3$, $R^6$ = Br $R^6$ = H $\xrightarrow{[Br]}$ $R^6$ = Br

*FIG. 1*

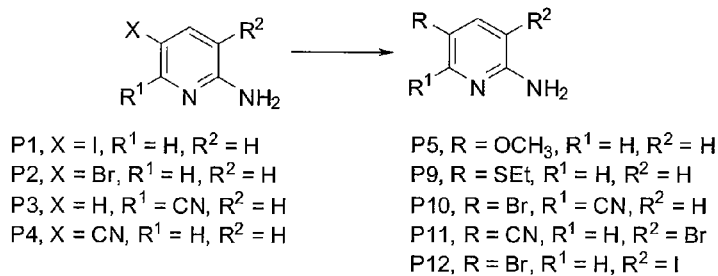

P1, X = I, $R^1$ = H, $R^2$ = H
P2, X = Br, $R^1$ = H, $R^2$ = H
P3, X = H, $R^1$ = CN, $R^2$ = H
P4, X = CN, $R^1$ = H, $R^2$ = H

P5, R = $OCH_3$, $R^1$ = H, $R^2$ = H
P9, R = SEt, $R^1$ = H, $R^2$ = H
P10, R = Br, $R^1$ = CN, $R^2$ = H
P11, R = CN, $R^1$ = H, $R^2$ = Br
P12, R = Br, $R^1$ = H, $R^2$ = I

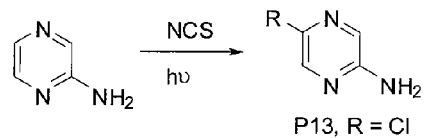

P13, R = Cl

*FIG. 2*

T1, R³ = H, R⁶ = H, R⁴ = CH₃, R⁸ = CH₂CONH₂
T2, R³ = H, R⁶ = CH₃, R⁴ = CH₃, R⁸ = CH₂CONH₂
T3, R³ = H, R⁶ = H, R⁴ = CH₃, R⁸ = CH₂CH₂OH
T4, R³ = H, R⁶ = CH₃, R⁴ = CH₃, R⁸ = CH₂CH₂OH
T5, R³ = H, R⁶ = CH₃, R⁴ = CH₃, R⁸ = CH₂C₆H₄OCH₃
T6, R³ = H, R⁶ = CH₃, R⁴ = CH₃, R⁸ = CH₃
T8, R³ = CH₃, R⁶ = H, R⁴ = CH₃, R⁸ = CH₂CONH₂
T9, R³ = CH₃, R⁶ = H, R⁴ = CH₃, R⁸ = CH₂CH₂OH

BETA-AMYLOID PET IMAGING AGENTS

CROSS REFERENCE TO RELATED APPLICATION

This application is a U.S. National Stage of PCT/US2007/066939 filed Apr. 19, 2007, which claims the benefit of U.S. Provisional Patent Application No. 60/793,807, filed Apr. 21, 2006, the contents of which are incorporated herein by reference in their entirety.

BACKGROUND OF THE INVENTION

All publications cited herein, including patents and published articles, are hereby incorporated herein by reference.

Alzheimer's disease (AD) is the most common cause of dementia and is characterized by progressive impairment in cognitive function and behavior. This progressive, irreversible brain disorder affects millions of lives and imposes a devastating burden on the health care around the world. Over the past two decades, significant progress has been made in deciphering the pathogenesis and developing new therapeutic approaches. The pathological features of AD include neuritic plaques composed of amyloid-β peptide (Aβ) fibrils, neurofibrillary tangles of hyper-phosphorylated tau, and neurotransmitter deficits. Recent efforts of managing AD have been focused on the prevention of production, aggregation, and deposition of amyloid-β peptides in the brain and the acceleration of clearance of Aβ from the brain.

Non-invasive detection and quantitation of amyloid deposits in the brain has been used to develop anti-amyloid therapies. Direct imaging of amyloid load in vivo in patients with AD is useful for the early diagnosis of AD and the development and assessment of treatment strategies. To this end, compounds suitable for in vivo imaging of amyloid deposits in human brains have been developed. Among these compounds are monoclonal antibodies against Aβ and peptide fragments, but these have had limited uptake by the brain when tested in patients with AD. Putrescine-gadolinium-Aβ has been injected into transgenic mice overexpressing amyloid, and this has resulted in labeling observed with MRI. Amyloid deposition can also be non-invasively imaged and quantitated with a radiotracer that readily enters the brain and selectively binds to amyloid deposits.

The small molecule approach for amyloid imaging has so far been the most successful. Some of the promising compounds that have been used to image amyloid are based on Congo red, thioflavin, stilbene, and FDDNP. The binding of different derivatives of Congo red and thioflavin has been studied in human autopsy brain tissue and in transgenic mice. Two compounds in advanced testing, fluorine-18-labelled-FDDNP(2-(1-{6-[(2-[$^{18}$F]fluoroethyl)(methyl)amino]-2-naphthyl}ethylidene)malononitrile) and carbon-11-labelled-PIB(6-hydroxy-2-(4'-methylaminophenyl)benzothiazole; Pittsburg compound B), both show more binding in the brains of patients with AD than in those of healthy people. Table 1 below, which is taken from Nordberg, A., "PET imaging of amyloid in Alzheimer's disease," *The Lancet Neurology* 3(9), September 2004, pp. 519-527, provides a list of compounds presently undergoing evaluation as amyloid imaging agents.

TABLE 1

Prior Art Compounds Used for Imaging of Amyloid in the Brains of Living Organisms
(reference numerals refer to citations in the Nordberg paper)

| Reference | Imaging compound | Imaging technique | Study |
|---|---|---|---|
| Friedland et al.[40] | $^{99}$Tc-10H3 | SPECT | Patients with AD |
| Shoghi-Jadid et al.[41] | $^{18}$F-FDDNP | PET | Patients with AD |
| Klunk et al.[39] | $^{11}$C-PIB | PET | Patients with AD |
| Mathis et al.[42] | $^{11}$C-BTA-1 | PET | Baboons |
| Poduslo et al.[43] | MION-Aβ$_{1-40}$ | MRI | Mice PS |
| Poduslo et al.[43] | PUT-Gd-Aβ | MRI | Mice PS |
| Wadghiri et al.[44] | Gd-DTPA-Aβ$_{1-40}$ | NMRi | Mice APP/PS |
| Mathis et al.[45] | BTA-1 | Multiphoton | Mice APP/PS |
| Bacskai et al.[46] | Thioflavin-S | Multiphoton | Mice APP |
| Bacskai et al.[46] | PIB | Multiphoton | Mice APP |

Two tertiary amines, [$^{18}$F]FEM-IMPY[N-(2-fluoroethyl)-4-(6-iodo-H-imidazo[1,2-a]pyridin-2-yl)-N-methylbenzeneamine], and its 3-fluoropropyl analog, [$^{18}$F]FPM-IMPY, have been previously evaluated by inventors herein as β-amyloid radioligands and reported in Cai, L., et al., "Synthesis and evaluation of two $^{18}$F-labeled 6-iodo-2-(4'-N,N-dimethylamino)phenylimidazo[1,2-a]pyridine derivatives as prospective radioligands for beta-amyloid in Alzheimer's disease," *J. Med. Chem.* 2004, 47, 2208-2218. After intravenous injection of either radioligand into rodent or monkey there is rapid and high uptake of radioactivity into brain with an SUV (standardized uptake value, % I.D.kg/g) of about 160 followed by biphasic clearance with a fast and a very slow component. These radioligands were rapidly metabolized by processes involving de-alkylation of the tertiary aromatic amino group, culminating in defluorination and high uptake of radioactivity in bone. Tetra-deuteration of the fluoroethyl group did not lead to a significant reduction in the residual brain radioactivity, but reduced the bone uptake of radioactivity, presumably due to an isotope effect on metabolism. An object of the present invention is to provide radioligands that do not undergo rapid defluorination and do not produce residual radioactivity in the brain. The invention therefore resides in further analogs of imidazo[1,2-a]pyridine (IMPY) useful as radioligands for the detection of Aβ amyloid aggregates in Alzheimer's Disease (AD) patients. Preferred among these analogs are imidazo[1,2-a]pyridine N-methylbenzeneamines in which a methyl group or a group similar in size to a methyl group (such as a bromine atom) is bonded to the ortho ring position nearest to the amine.

The effective management of Alzheimer's disease requires tools to diagnose, monitor, treat and prevent the disease. An object of the present invention is therefore to provide amyloid imaging agents with high specificity of binding to beta amyloid, low background noise, better entry into brains, and improved labeling efficiencies.

THE INVENTION

Two novel classes of amyloid imaging agents are disclosed herein. The first class are derivatives of imidazopyridinylbenzeneamine (IMPY), and are defined by Formula (I):

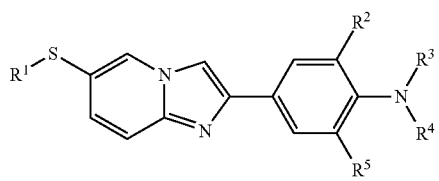

In Formula (I):
- $R^1$ is $C_1$-$C_6$ alkyl, or aryl-, or halo-substituted $C_1$-$C_6$ alkyl methyl; preferably $C_1$-$C_6$ alkyl or fluoro-substituted $C_1$-$C_6$ alkyl; and most preferably methyl, ethyl, fluoromethyl, or fluoroethyl,
- $R^2$ is H, $C_1$-$C_6$ alkyl, halo-substituted $C_1$-$C_6$ alkyl, halo, or $C_1$-$C_6$ alkylthio, and $R^3$ is H or $C_1$-$C_6$ alkyl, or $R^2$ and $R^3$ are joined to form a thio-$C_1$-$C_3$ alkylene linkage (—S-alkyl-) linkage or alkylene linkage between the 2-position (to which $R^2$ is attached in the formula) on the phenyl ring and the amine nitrogen (to which $R^3$ is attached) with the S atom attached to the 2-position carbon; and preferably $R^2$ is hydrogen, bromo, or methylthio, $R^3$ is hydrogen or methyl, or $R^2$ and $R^3$ are joined to form a thiomethylene (—SCH$_2$—) linkage between the 2-position (to which $R^2$ is attached in the formula) on the phenyl ring and the amine nitrogen (to which $R^3$ is attached) with the S atom attached to the 2-position carbon, and
- $R^4$ is H or $C_1$-$C_3$ alkyl, and $R^5$ is H or $C_1$-$C_3$ alkyl, or $R^4$ and $R^5$ are joined to form a $C_1$-$C_3$ alkylenethio linkage (-alkyl-S—) linkage between the amine nitrogen (to which $R^4$ is attached) and the 6-position (to which $R^5$ is attached in the formula) on the phenyl ring with the S atom attached to the 2-position carbon; and preferably $R^4$ is H and $R^5$ is H, or $R^4$ and $R^5$ are joined to form a methylenethio (—CH$_2$S—) linkage between the amine nitrogen (to which $R^4$ is attached) and the 6-position (to which $R^5$ is attached in the formula) on the phenyl ring with the S atom attached to the 2-position carbon.

TABLE 1

Examples of compounds within the scope of Formula (I) are:

| Example | $R^1$ | $R^2$ | $R^3$ | $R^4$ | $R^5$ |
|---|---|---|---|---|---|
| 1.1 | CH$_3$ | H | CH$_3$ | H | H |
| 1.2 | C$_2$H$_5$ | H | CH$_3$ | H | H |
| 1.3 | CH$_3$ | Br | H | H | H |
| 1.4 | FCH$_2$ | H | CH$_3$ | H | H |
| 1.5 | FCH$_2$ | Br | H | H | H |
| 1.6 | FCH$_2$CH$_2$ | H | CH$_3$ | H | H |
| 1.7 | FCH$_2$CH$_2$ | Br | H | H | H |
| 1.8 | FCH$_2$ | SCH$_3$ | H | H | H |
| 1.9 | FCH$_2$ | SCH$_2$ | | H | H |
| 1.10 | FCH$_2$ | SCH$_2$ | | SCH$_2$ | |

The second class are derivatives of benzothiazolylbenzeneamine (BTA), and are defined by Formula (II):

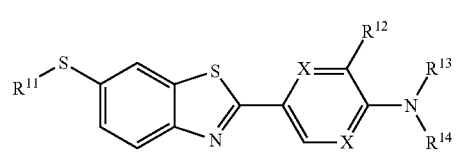

In Formula (II):
- $R^{11}$ is $C_1$-$C_6$ alkyl, halo-substituted $C_1$-$C_6$ alkyl, hydroxy-substituted $C_1$-$C_6$ alkyl, or carbamoyl $C_1$-$C_6$ alkyl; preferably $C_1$-$C_3$ alkyl, fluoro-substituted $C_1$-$C_3$ alkyl, hydroxy-substituted $C_1$-$C_3$ alkyl, or carbamoyl $C_1$-$C_3$ alkyl; and most preferably methyl, ethyl, fluoromethyl, fluoroethyl, hydroxymethyl, hydroxyethyl, carbamoylmethyl, or carbamoylethyl;
- $R^{12}$ is H, $C_1$-$C_6$ alkyl, halo-substituted $C_1$-$C_6$ alkyl, halo, and $C_1$-$C_6$ alkylthio, and $R^{13}$ is a member selected from the group consisting of H and $C_1$-$C_6$ alkyl, or $R^{12}$ and $R^{13}$ are joined to form a thio-$C_1$-$C_3$ alkylene linkage (—SCH$_2$—) between the 2-position (to which $R^{12}$ is attached in the formula) on the phenyl ring and the amine nitrogen (to which $R^{13}$ is attached) with the S atom attached to the 2-position carbon; preferably H, $C_1$-$C_3$ alkyl, chloro, bromo, chloro-substituted $C_1$-$C_3$ alkyl, bromo-substituted $C_1$-$C_3$ alkyl, and $C_1$-$C_3$ alkylthio, and $R^{13}$ is a member selected from the group consisting of H and $C_1$-$C_3$ alkyl, or $R^{12}$ and $R^{13}$ are joined to form a thiomethylene linkage (—SCH$_2$—) between the 2-position (to which $R^{12}$ is attached in the formula) on the phenyl ring and the amine nitrogen (to which $R^{13}$ is attached) with the S atom attached to the 2-position carbon; and most preferably $R^{12}$ is hydrogen, bromo, or methylthio, $R^{13}$ is hydrogen or methyl, or $R^{12}$ and $R^{13}$ are joined to form a thiomethylene (—SCH$_2$—) linkage between the 2-position (to which $R^{12}$ is attached in the formula) on the phenyl ring and the amine nitrogen (to which $R^{13}$ is attached) with the S atom attached to the 2-position carbon, and
- $R^{14}$ is H or $C_1$-$C_6$ alkyl, preferably H or methyl, and
- X is CH or N.

TABLE 2

Examples of compounds within the scope of Formula (II) are:

| Example | $R^{11}$ | $R^{12}$ | $R^{13}$ | $R^{14}$ | X |
|---|---|---|---|---|---|
| 2.1 | CH$_3$ | H | CH$_3$ | H | N |
| 2.2 | H$_2$N—C(O)—CH$_2$ | H | CH$_3$ | H | CH |
| 2.3 | HOC$_2$H$_4$ | Br | H | H | CH |
| 2.4 | FCH$_2$ | H | CH$_3$ | H | N |
| 2.5 | FCH$_2$ | Br | H | H | N |
| 2.6 | FCH$_2$CH$_2$ | H | CH$_3$ | H | N |
| 2.7 | FCH$_2$CH$_2$ | Br | H | H | N |
| 2.8 | FCH$_2$ | SCH$_3$ | H | H | N |
| 2.9 | FCH$_2$ | SCH$_2$ | | H | N |
| 2.10 | FCH$_2$ | SCH$_2$ | | CH$_3$ | N |

This invention resides in the above compounds as novel imaging agents for the imaging of amyloid deposits, new methods of synthesis of imidazopyridinylbenzeneamine (IMPY) derivatives, and methods for diagnosing Alzheimer's disease in vivo by positron emission tomography, magnetic resonance imaging and other imaging methods involving the use of the imaging agents of this invention.

EXAMPLES

Materials and methods
Preparation of Compounds
Chemicals and Reagents. Common reagents used in the syntheses were purchased from Aldrich Chemical Company, Fluka Chemical Company (Milwaukee, Wis.), Acros (Hampton, N.H.), or Strem Chemicals (Newburyport, Mass.), and were used without further purification, unless otherwise indicated. DiPPF[1,1'-bis(diisopropylphosphino)ferrocene] and hexamethylditin were from Strem Chemicals. 2-Mercaptoethanol, 5-iodopyridin-2-amine, 5-bromopyridin-2-amine, pyrazin-2-amine, 2-bromoacetyl bromide, o-toluidine, 1-(4-aminophenyl)ethanone, N-methyl-N-(trimethylstannyl)methanamine, sodium methoxide, and $Pd_2dba_3$ (dipalladium dibenzylideneacetone), were from Aldrich. 2-mercaptoacetamide and 6-aminopyridine-3-carbonitrile (P4) were from Acros. Water was purified through a Millipore water purification system, comprising a combination of two filters, one Rio™, one reservoir, and one Milli-Q® synthesis system (Bedford, Mass.). Common solvents were obtained from Fisher Scientific (Pittsburgh, Pa.). Brain tissue from deceased Alzheimer's Disease (AD) patients was obtained from Brain Bank of the Clinical Brain Disorders Branch, National Institute of Mental Health, National Institutes of Health.

1-(4-(methylamino)phenyl)ethanone(2),[2] 1-(4-amino-3-bromophenyl)ethanone(3), N,2-dimethylbenzenamine(K2), 2,2,2-trifluoro-N-o-tolylacetamide (A3), N-o-tolylacetamide (A4), 6-aminopyridine-2-carbonitrile(P3), 6-amino-5-bromopyridine-3-carbonitrile(P11), 5-bromo-3-iodopyridin-2-amine(B3), were synthesized as reported in the literature.

Instrument and general conditions. Analytical HPLC was performed using a reverse phase column (X-Tera C18; 5 µm; 10.0×250 mm; Waters) eluted with c. ammonia (0.25%) in acetonitrile-water at 6.2 mL/min. The chromatography system was fitted with a continuous wavelength UV-vis detector (Beckman System Gold 168 Detector) and an autosampler (Beckman System Gold 508 Autosampler). For semi-preparative Beckman HPLC, a reverse phase column (X-Tera C18; 5 µm; 19×250 mm; Waters) was eluted at 20.0 mL/min. The HPLC system was fitted with a manual injector (5 mL injection loop) and a third delivery pump using acetonitrile as eluant at 1 mL/min. The purity of compounds was determined with HPLC monitored for UV absorbance at 280 nm (for IMPY derivatives) or 254 nm (for other aromatic compounds) and expressed as area percentage of all peaks. The $^1H$ and $^{13}C$ NMR spectra of all compounds were acquired on a Jeol GSX 270 (270 MHz $^1H$ and 68 MHz $^{13}C$), on a Bruker DRX 300 (300 MHz $^1H$ and 75 MHz $^{13}C$), on a Bruker DRX 400 (400 MHz $^1H$ and 100 MHz $^{13}C$) and on a Bruker AM500 (500 MHz $^1H$ and 125 MHz $^{13}C$), using the chemical shifts of residual deuterated solvent as the internal standard; chemical shift (δ) data for the proton and carbon resonance were reported in parts per million (ppm) relative to the internal standard. Thin-layer chromatography (TLC) was performed using Silica Gel 60 F254 plates from EM Science and compounds visualized under UV light at either 250 or 360 nm. Flash chromatography was carried out using a Biotage Horizon™ HPFC™ system (Charlottesville, Va., column sizes: 12 mm×150 mm, 25 mm×150 mm, 40 mm×150 mm) with hexanes and ethyl acetate (EtOAc) as eluents with chromatographic solvent proportions expressed on a volume: volume basis. IR spectra were recorded using a Perkin-Elmer Spectrum One FT-IR spectrometer, and UV/vis spectra were recorded using a Lambda 40 UV/vis spectrometer. Mass spectra were acquired using either Thermo Finnigan $LCQ^{DECA}$ (MS-HPLC column: Luna C18; 5 µm 2.0×150 mm; Phenomenex, flow rate: 150 µL/min, eluent: MeOH and $H_2O$ mixture) or Thermo Finnigan PolarisQ GC-MS (GC column: capillary RTX-5 ms 30 m×0.25 mm, flow rate: 1 mL/min, carrier gas: He), or VG Micromass 7070E and AutoSpec-Q spectrometers. High-resolution mass spectra (HRMS) were acquired from Mass Spectrometry Laboratory, University of Illinois at Urbana-Champaign (Urbana, Ill.). Elemental analyses of selected compounds were carried out by Midwest Microlab (Indianapolis, Ind.) or Galbraith Laboratories, Inc. (Knoxville, Tenn.), or Mr Stephen Boyer, SACS, University of London. The melting points were measured using Electrothermal Mel-Temp Manual Melting Point Apparatus (Fisher Scientific), and uncorrected. A CEM Discover microwave system was used for microwave synthesis (Matthews, N.C.).

The following syntheses are illustrated by molecular formulas and reaction schemes in the Figures attached hereto, and the structures represented by the acronyms and other symbols used below for the various intermediates and compounds are shown in the Figures.

1-(3-bromo-4-(methylamino)phenyl)ethanone (K3). The compound was synthesized by bromination of the aryl amine by NBS (N-Bromosuccinimide).

The following are syntheses of ketones and α-bromoketones according to FIG. 1 as intermediates in the preparation of the IMPY derivatives.

N-(4-acetyl-2-methylphenyl)-2,2,2-trifluoroacetamide (K4). 2,2,2-trifluoro-N-o-tolylacetamide (8.0 g; 39.4 mmol) was dissolved in 20 mL $CS_2$. Bromoacetic bromide (8.4 g; 68.3 mmol) was added dropwise. $AlCl_3$ (16.0 g; 120 mmol) was added in portions, with drying tube attached to the reaction flask. The reaction mixture was refluxed overnight. After reaction, the solvent was removed. Ice and water were added, and some yellow solid precipitated. The solid was isolated by filtration, and purified by silica gel column chromatography, to afford 3.8 g (yield 39%) of product as off-white solid. $^1H$ NMR (300 MHz; $CDCl_3$), δ 8.30 (s, 1H, Ar—H), 7.91 (brs, 1H, NH), 7.81 (d, $^3J_{HH}$=8.2 Hz, 1H, Ar—H), 7.36 (d, $^3J_{HH}$=7.9 Hz, 1H, Ar—H), 2.60 (s, 3H, $COCH_3$), 2.36 (s, 3H, $CH_3$).

N-(4-acetyl-2-bromophenyl)-2,2,2-trifluoroacetamide (K5). 1-(4-aminophenyl)ethanone (2.50 g; 18.5 mmol) was dissolved in 100 mL toluene. NBS (3.30 g; 18.8 mmol) was added portionwise. After 15 min stirring at RT, the organic phase was washed with water twice, and dried over $Na_2SO_4$. The solvent was removed by rotavap to get oil, which was purified by silica gel chromatography, to afford 1.7 g of a white solid, 1-(4-amino-3-bromophenyl)ethanone (1.7 g; 7.94 mmol). The intermediate was dissolved in $CH_2Cl_2$. The reaction mixture was cooled to 0° C. Trifluoroacetic anhydride (2.0 g; 9.52 mmol) and $NEt_3$ (1.0 g; 9.90 mmol) were added sequentially. The reaction mixture was stirred at RT for another hour. The organic phase was washed twice with water, dried over $MgSO_4$. The solvent was removed, to afford 2.4 g (yield 42%) of product as white solid. $^1H$ NMR (400 MHz, $CDCl_3$) δ 8.61 (s, 1H, N—H), 8.46, (d, $^3J_{HH}$=8.6 Hz, 1H, Ar—H), 8.21 (d, $^4J_{HH}$=2.0 Hz, 1H, Ar—H), 7.95 (dd, $^3J_{HH}$=8.6 Hz, $^4J_{HH}$=1.9 Hz, 1H, Ar—H), 2.58 (s, 3H, $CH_3$).

N-(4-acetyl-2-bromophenyl)-2,2,2-trifluoro-N-methylacetamide (K6). 1-(3-bromo-4-(methylamino)phenyl)ethanone (1.4 g; 6.14 mmol) was dissolved in 15 mL $CH_2Cl_2$. The reaction mixture was cooled to 0° C. Trifluoroacetic anhydride and $Et_3N$ were added sequentially. The mixture was stirred at RT for 3 hrs, washed with water three times, and dried over $Na_2SO_4$. The solvent was removed, and product was dried to afford 1.9 g (yield 96%) of a yellow solid. $^1H$ NMR (300 MHz; $CDCl_3$), δ 8.13 (s, 1H, Ar—H), 7.83 (d, $^3J_{HH}$=8.8 Hz, 1H, Ar—H), 7.02 (d, $^3J_{HH}$=8.6 Hz, 1H, Ar—H), 2.91 (s, 3H, $NCH_3$), 2.53 (s, 3H, $COCH_3$).

N-(4-(2-bromoacetyl)-2-methylphenyl)-2,2,2-trifluoroacetamide (B2). 2,2,2-trifluoro-N-o-tolylacetamide (5.0 g; 24.6 mmol) was dissolved in 20 mL $CS_2$. The mixture was cooled below 10° C. Bromoacetic bromide (10.1 g; 50.0 mmol) was added dropwise. $AlCl_3$ (10.0 g; 75.0 mmol) was added in portions, with drying tube attached to the reaction flask. The reaction mixture was refluxed overnight. After the reaction is complete as monitored by TLC, the upper $CS_2$ layer was removed. The lower layer was added into 7.0 mL ice water mixed with HCl. The product was extracted into $CH_2Cl_2$, and dried over $MgSO_4$. The solvent was removed, and the solid was dried to afford 5.0 g of crude product, which was purified by silica gel column chromatography, to afford 3.0 g (yield 38%) of product as yellow solid. $^1$H NMR (300 MHz; $CDCl_3$), δ 8.40 (s, 1H, Ar—H), 7.87 (brs+d, $^3J_{HH}$=8.0 Hz, 2H, Ar—H), 7.43 (d, $^3J_{HH}$=8.0 Hz, 1H, Ar—H), 4.46 (s, 2H, $COCH_2Br$), 2.41 (s, 3H, $CH_3$).

N-(4-(2-bromoacetyl)-2-methylphenyl)-N-methylacetamide (B3). $^1$H NMR (300 MHz; $CDCl_3$), δ 7.89 (dd, $^3J_{HH}$=8.0 Hz, $^4J_{HH}$=1.7 Hz, 1H, Ar—H), 7.78 (d, $^4J_{HH}$=1.7 Hz, 1H, Ar—H), 7.45 (d, $^3J_{HH}$=8.0 Hz, 1H, Ar—H), 4.41 (AB, $^2J_{HH}$=11.7 Hz, 2H, $COCH_2Br$), 3.20 (s, 3H, $NCH_3$), 2.33 (s, 3H, Ar—$CH_3$), 1.78 (s, 3H, $COCH_3$).

N-(2-bromo-4-(2-bromoacetyl)phenyl)-2,2,2-trifluoroacetamide (B4). N-(4-acetyl-2-bromophenyl)-2,2,2-trifluoroacetamide (12.1 g; 39.0 mmol) and tetrabutylammonium tribromide (18.8 g; 39.0 mmol) were dissolved separately in ethanol. After combination, and refluxing for 4 hrs, there was precipitate formation. The solvent was removed. $NaHCO_3$ solution was added to neutralize any residue acid. The solid was filtered, and washed with $CH_2Cl_2$, to afford 7.0 g (yield 46%) of product as pale green solid. $^1$H NMR (400 MHz, $CDCl_3$) δ 8.64 (s, 1H, N—H), 8.51 (d, $^3J_{HH}$=8.6 Hz, 1H, Ar—H), 8.25 (d, $^4J_{HH}$=2.0 Hz, 1H, Ar—H), 7.98 (dd, $^3J_{HH}$=8.6 Hz, $^4J_{HH}$=2.0 Hz, 1H, Ar—H), 4.38 (s, 2H, —$CH_2$—Br).

N-(2-bromo-4-(2-bromoacetyl)phenyl)-2,2,2-trifluoro-N-methylacetamide (B5). $CuBr_2$ (6.0 g; 26.9 mmol) was suspended in 20 mL ethyl acetate. The mixture was heated to reflux. N-(4-acetyl-2-bromophenyl)-2,2,2-trifluoro-N-methylacetamide (4.5 g; 13.9 mmol) dissolved in 20 mL $CHCl_3$ was added. The mixture was refluxed for 4 hrs, and filtered. The solvent was removed from the filtrate to get an orange solid, which was purified by silica gel column chromatography using the mixture of ethyl acetate and petroleum ether from 1:100 to 1:50, to afford 1.9 g (yield 34%) of product as yellow solid. $^1$H NMR (400 MHz, $CDCl_3$) δ Isomer α (80%) 8.33 (d, $^4J_{HH}$=2.0 Hz, 1H, Ar—H), 8.02 (dd, $^3J_{HH}$=8.2 Hz, $^4J_{HH}$=2.0 Hz, 1H, Ar—H), 7.48 (dd, $^3J_{HH}$=8.2 Hz, $^5J_{HH}$=0.5 Hz, 1H, Ar—H), 4.46 (AB, $^2J_{HH}$=11.8 Hz, 1H, $CH_2$), 4.42 (AB, $^2J_{HH}$=11.8 Hz, 1H, $CH_2$), 3.36 (d, $^4J_{HF}$=0.4 Hz, 3H, $CH_3$). Isomer β (20%) 8.33 (d, $^4J_{HH}$=2.0 Hz, 1H, Ar—H), 8.05 (dd, $^3J_{HH}$=8.2 Hz, $^4J_{HH}$=2.0 Hz, 1H, Ar—H), 7.44 (dd, $^3J_{HH}$=8.2 Hz, $^5J_{HH}$=0.5 Hz, 1H, Ar—H), 4.46 (AB, $^2J_{HH}$=11.8 Hz, 1H, $CH_2$), 4.42 (AB, $^2J_{HH}$=11.8 Hz, 1H, $CH_2$), 3.49 (q, $^4J_{HF}$=1.6 Hz, 3H, $CH_3$).

Figure 4:
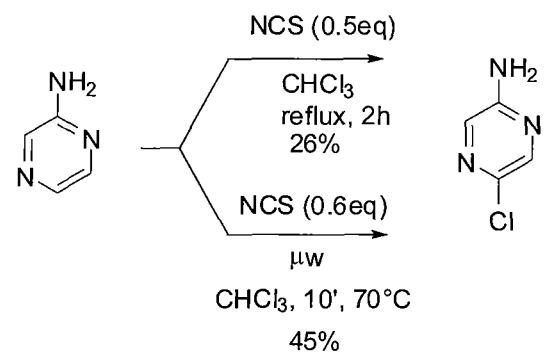

The following are syntheses of 2-aminopyridine derivatives according to FIGS. 2, 3, and 4 as further intermediates in the preparation of the IMPY derivatives and the IMPY derivatives themselves.

5-methoxypyridin-2-amine (P5). Method a: 2-Amino-4-bromopyridine (0.10 g; 0.58 mmol), sodium methoxide (0.16 g; 2.9 mmol) and copper powder nanosized activated (0.11 g; 1.74 mmol) were introduced in a screw cap vial (Pyrex glass) together with 2.0 mL of anhydrous MeOH and a stirrer bar. The vial was closed and put in an oil bath at 135° C. and stirred for 14 h. The mixture was cooled, diluted with MeOH (5.0 mL) and filtered through an SPE silica gel cartridge and the product eluted with AcOEt. The fractions were collected and evaporated obtaining a crude of 92 mg of product which was further purified by FCC (DCM/AcOEt=1:1) to give 26 mg (yield 36%) of the title compound as brown oil. Method b: 2-Amino-4-bromopyridine (0.10 g; 0.58 mmol), sodium methoxide (0.16 g; 2.9 mmol) and copper powder nanosized activated (0.11 g; 1.74 mmol) were introduced in a microwave glass tube with 1.5 mL of anhydrous DMF and sealed. The tube was introduced in the microwave cavity and heated for 30 min at 140° C. (140 C30 M75 W300 Psi). Although DMF is a high boiling solvent, high pressure was observed, probably caused by the partial methanolysis of the DMF resulting in low boiling products such as methyl formate and dimethylamine. The mixture was diluted with 10 mL of 2 M $NH_4Cl$ solution and extracted 3 times with AcOEt. The organic phase was washed 2 times with 2 M $NH_4Cl$ solution and 1 time with water to remove the remaining DMF, dried on $NaSO_4$, and filtered. After the solvent was removed, the crude product was purified by FCC (AcOEt) to afford 12 mg (yield 17%) of the title compound as brown oil. $^1$H NMR (270 MHz; $CDCl_3$), δ 7.74 (1H, d, $^3J_{HH}$=3.0 Hz), 7.06 (1H, dd, $^3J_{HH}$=9.0 Hz, $^4J_{HH}$=3.0 Hz), 6.45 (1H, d, $^3J_{HH}$=9.0 Hz), 3.95 (2H, bs, $NH_2$), 3.74 (3H, s, $OCH_3$); m/z (EI-MS): 124 ($M^+$), 109 ($[M-CH_3]^+$).

5-(ethylthio)pyridin-2-amine (P9). 2-Amino-5-iodo-pyridine (2.20 g; 10 mmol), sodium ethanethiolate 80% (1.7 g; 16 mmol) and copper powder (190 mg; 3.00 mmol) were loaded into a 100 mL round bottom flask under nitrogen. Ethylene glycol (40 mL; 0.25 mol) was added and the solution stirred at 150° C. for 26 h. The cooled solution was filtered and partitioned between ethyl acetate and water twice. The organic layer was dried over barium oxide, filtered and the solvent removed in vacuo to afford 1.2 g (yield 76%) of product as yellow oil. $^1$H-NMR (300 MHz; $CDCl_3$), δ 8.06 (1H, d, $^4J_{HH}$=2.1 Hz, Ar—H), 7.48 (1H, dd, $^3J_{HH}$=8.7 Hz, $^4J_{HH}$=2.4 Hz, Ar—H), 6.42 (1H, dd, $^3J_{HH}$=8.7 Hz, $^5J_{HH}$=0.6 Hz, Ar—H), 2.68 (2H, q, $^3J_{HH}$=7.3 Hz, $CH_2$), 1.15 (3H, t, $^3J_{HH}$=7.2 Hz, $CH_3$).

6-amino-3-bromopyridine-2-carbonitrile (P10). $^1$H NMR (300 MHz; DMSO-$d_6$), δ 7.75 (d, $^3J_{HH}$=9.1 Hz, 1H, Ar—H), 6.69 (d, $^3J_{HH}$=9.1 Hz, 1H, Ar—H).

5-chloropyrazin-2-amine (P13). Method a: In a double necked dry flask equipped with condenser and dropping funnel, under nitrogen flow, were added 2-amino-pyrazine (0.50 g, 5.25 mmol) and 13 mL of anhydrous $CHCl_3$ previously passed on basic $Al_2O_3$. This solution was heated at 60° C. under stirring. A solution of NCS (0.35 g, 2.12 mmol) in 7 mL of the anhydrous $CHCl_3$ was added to the mixture through dropping funnel during 1.5 hr. After another 30 minutes, the reaction was stopped and the solvent evaporated. The residue was dissolved in methanol and absorbed on silica (2 g). This crude product was purified by FCC (Hexane/DCM/AcOEt=1:1:1) to afford 73 mg (yield 26%) of product as yellow solid. Method b: 2-Amino-pyrazine (0.10 g, 1.05 mmol) and NCS (80 mg, 0.60 mmol) were added in a microwave tube with 1.5 mL of the anhydrous $CHCl_3$ and sealed. The tube was placed in the microwave cavity and heated at 70° C. for 10 min. (70 C10 M60 W300 Psi). After the work-up, the crude (0.15 g) was purified by FCC (Hexane/DCM/AcOEt=1:1:1) to afford 35 mg (yield 45%) of the product as yellow solid. $^1$H NMR (270 MHz; $d_6$-DMSO), δ 7.99 (1H, s, H-6), 7.67 (1H, s, H-3), 6.65 (2H, bs, $NH_2$). m/z (EI-MS): 129 ($M^+$), 99, 94 ($[M-Cl]^+$).

4-(6-chloro-H-imidazo[1,2-a]pyridin-2-yl)-N,N-dimethylbenzenamine (L5). 2-Bromo-1-(4-(dimethylamino)phenylethanone (11) (1.21 g; 5.00 mmol) and 5-chloro-2-aminopyridine (7c) (0.668 g; 5.20 mmol) were used to give 12c (0.65 g; yield 48%); Mp: 234-236° C.; $^1$H NMR (400 MHz, $CDCl_3$) δ 8.10 (s, 1H, Ar—H), 7.76 (d, $^3J_{HH}$=8.9 Hz, 2H, Ar—H), 7.65 (s, 2H, Ar—H), 7.14 (d, $^3J_{HH}$=9.2 Hz, 1H, Ar—H), 6.71 (d, $^3J_{HH}$=8.6 Hz, 2H, Ar—H), 2.95 (s, 6H, $CH_3$). $^{13}C^{13}$ NMR (400 MHz, $CDCl_3$) δ 149.3, 146.2, 142.6, 125.8 (s, 2C), 124.2, 121.8, 120.0, 118.8, 116.0, 111.2 (s, 2C), 105.7, 39.2 (s, 2C, NCH$_3$). m/z (ES-MS): 275.1 (4%), 274.1 (51%), 273.1 (18%), 272.1 (100%, [M+H]$^+$). HRMS m/z (TOF$^+$): Calc. C$_{15}$H$_{15}$N$_3$Cl=272.0955. Found: 272.0960. Error (ppm): +1.8.

4-(6-fluoro-H-imidazo[1,2-a]pyridin-2-yl)-N,N-dimethylbenzenamine (L6). 2-Bromo-1-(4-(dimethylamino)-phenylethanone (11) (1.21 g; 5.00 mmol) and 5-fluoro-2-aminopyridine (7d) (0.583 g; 5.17 mmol) were stirred in reflux ethanol (50 mL) for 4 h. Pale yellow precipitate formed. NaHCO$_3$ (0.41 g; 4.9 mmol) was added to the reaction mixture after cooling (15 min.). The mixture was refluxed again for another 2 h. After cooling, the solvents were removed. The solid was washed with water, CH$_2$Cl$_2$, and recrystallized from ethyl acetate, to get 0.42 g of product. Yield 33%. Mp: 228-229 °C.; $^1$H NMR (400 MHz, CD$_3$OD) δ 8.35 (m, $^3$J$_{FH}$=4.2 Hz, $^4$J$_{HH}$=2.4 Hz, $^5$J$_{HH}$=0.7 Hz, 1H, Ar—H), 7.93 (d, $^4$J$_{HH}$=0.3 Hz, 1H, Ar—H), 7.66-7.62 (m, 2H, Ar—H), 7.41 (m, $^3$J$_{HH}$=9.8 Hz, $^4$J$_{FH}$=5.0 Hz, $^5$J$_{HH}$=0.6 Hz, 1H, Ar—H), 7.14 (m, $^3$J$_{HH}$=9.8 Hz, $^3$J$_{FH}$=8.3 Hz, $^4$J$_{HH}$=2.4 Hz, 1H, Ar—H), 6.74-6.70 (m, 2H, Ar—H), 2.89 (s, 6H, CH$_3$). $^{13}$C NMR (400 MHz, CDCl$_3$) δ 153.2 (d, $^1$J$_{FC}$=236.4 Hz, 1C, Ar), 150.0 (s, 1C, Ar), 147.5 (s, 1C, Ar), 143.1 (s, 1C, Ar), 127.0 (s, 2C, Ar), 121.2 (s, 1C, Ar), 117.2 (d, $^3$J$_{FC}$=9.3 Hz, 1C, Ar), 116.0 (d, $^2$J$_{FC}$=25.4 Hz, 1C, Ar), 112.4 (s, 2C, Ar), 112.0 (d, $^2$J$_{FC}$=40.6 Hz, 1C, Ar), 107.9 (d, $^4$J$_{FC}$=1.8 Hz, 1C, Ar), 40.5 (s, 2C, CH$_3$). m/z (ES-MS): 257.1 (7%), 256.1 (100%, [M+H]$^+$). HRMS m/z (TOF$^+$): Calc. C$_{15}$H$_{15}$N$_3$F = 256.1250. Found: 256.1261. Error (ppm): +4.3.

N,N-dimethyl-4-(6-nitro-H-imidazo[1,2-a]pyridin-2-yl) benzenamine (L7). 2-Bromo-1-(4-(dimethylamino)phenylethanone (11) (0.40 g; 1.65 mmol) and 5-nitro-pyridin-2-amine (70 (0.30 g; 2.15 mmol) were stirred in reflux anhydrous acetonitrile (25 mL) at 90-95 °C. under dinitrogen for 2 h. NaHCO$_3$ (0.25 g; 2.97 mmol) was added to the reaction mixture after cooling (15 min). The mixture was refluxed for another 9 h. After cooling, the mixture was filtered through a Busch funnel. The precipitate was washed with acetonitrile and water, to afford 0.11 g of the red product. Yield 23%. Mp: 275-277° C.; NMR (400 MHz, DMSO-d$_6$) δ 9.77 (dd, $^4$J$_{HH}$=2.3 Hz, $^5$J$_{HH}$=0.8 Hz, 1H, Ar—H), 8.42 (s, 1H, Ar—H), 7.91 (dd, $^3$J$_{HH}$=9.8 Hz, $^4$J$_{HH}$=2.3 Hz, 1H, Ar—H), 7.83-7.80 (m, 2H, Ar—H), 7.68-7.65 (m, 1H, Ar—H), 6.83-6.80 (m, 2H, Ar—H), 2.97 (s, 6H, CH$_3$). $^{13}$C$^{13}$ NMR (400 MHz, DMSO-d$_6$) δ 150.6, 148.5, 144.9, 136.0, 127.3, 126.9 (s, 2C, Ar), 120.2, 118.4, 115.2, 112.2 (s, 2C, Ar), 109.3, 40.2 (s, 2C, CH$_3$). m/z (ES-MS): 284.1 (29%), 283.1 (100%, [M+H]$^+$). HRMS m/z (TOF$^+$): Calc. C$_{15}$H$_{15}$N$_4$O$_2$=283.1195. Found: 283.1206. Error (ppm): +3.9.

2-(4-(dimethylamino)phenyl)-H-imidazo[1,2-a]pyridine-6-carbonitrile (L8). The same method as described above was used. 2-Bromo-1-(4-(dimethylamino)phenylethanone (11) (1.21 g; 5.00 mmol) and 6-aminopyridine-3-carbonitrile (7e) (0.63 g; 5.3 mmol) were used to give 12e (0.85 g; yield 65%); Mp: 269-271° C.; $^1$HNMR (400 MHz, CDCl$_3$) δ 8.42 (dd, $^4$J$_{HH}$=1.6 Hz, $^5$J$_{HH}$=0.6 Hz, 1H, Ar—H), 7.76-7.73 (m, 2H, Ar—H), 7.72 (s, 1H, Ar—H), 7.58-7.55 (m, 1H, Ar—H), 7.15 (dd, $^3$J$_{HH}$=9.3 Hz, $^4$J$_{HH}$=1.7 Hz, 1H, Ar—H), 6.72-6.69 (m, 2H, Ar—H), 2.95 (s, 6H, CH$_3$). $^{13}$C$^{13}$ NMR (400 MHz, CDCl$_3$) δ 149.9, 148.1, 143.7, 129.9, 126.3 (s, 2C, Ar), 123.0, 119.2, 116.6, 115.8, 111.2 (s, 2C, Ar), 106.2, 96.9, 39.3 (s, 2C, CH$_3$). m/z (ES-MS): 364.0 (8%), 264.1 (29%), 263.1 (100%, [M+H]$^+$). HRMS m/z (TOF$^+$): Calc. C$_{16}$H$_{15}$N$_4$=263.1297. Found: 263.1303. Error (ppm): +2.3.

4-(6-methoxy-H-imidazo[1,2-a]pyridin-2-yl)-N,N-dimethylbenzenamine (L9). In a 2-necked round bottomed flask equipped with a condenser and under nitrogen flow were introduced the 2-amino-5-methoxypyridine (0.15 g, 1.17 mmol), the 2-bromo-4'-dimethylamino-acetophenone (0.31 g, 1.29 mmol) and 14 mL of absolute EtOH. The reaction mixture was stirred at reflux for 2 h. After it cooled down, NaHCO$_3$ (0.15 g, 1.75 mmol) was added, the mixture was refluxed for another 6 hrs. After the solvent was removed, the residue was dissolved in AcOEt. The organic phase was washed with water, dried over MgSO$_4$, and filtered. The solvent was removed to afford 0.271 g crude product, which was purified by FCC (DCM/AcOEt=1:1) to give 0.129 g (yield 41%) of the product as yellow solid. M.p.=177-179° C. $^1$H NMR (270 MHz; CDCl$_3$), δ 7.82 (d, $^3$J$_{HH}$=8.7 Hz, 2H, Ar—H), 7.71 (s, 1H, H-3), 7.65 (s, 1H, Ar—H), 7.53 (d, $^3$J$_{HH}$=9.6 Hz, 1H, Ar—H), 6.96 (dd, $^3$J$_{HH}$=9.6, $^4$J$_{HH}$=1.8, 1H, Ar—H), 6.81 (d, $^3$J$_{HH}$=8.8 Hz, 2H, Ar—H), 3.84 (s, 3H, OCH$_3$), 3.02 (s, 6H, NCH$_3$); $^{13}$C{$^1$H} NMR (125 MHz, CDCl$_3$), δ 151.0, 150.4, 149.2, 146.0, 143.0, 126.8 (Ph-2,6), 119.2 (C7), 117.0 (C8), 112.5 (Ph-3,5), 107.6 (C3), 106.2 (C5), 56.2 (OCH$_3$), 40.5 (NCH$_3$). m/z (EI-MS): 267 (M$^+$), 252 (M$^+$-CH$_3$); Calc. C$_{16}$H$_{17}$N$_3$O: C, 71.89; H, 6.41; N, 15.72. Found: C, 71.60; H, 6.62; N, 15.96.

2-(4-(dimethylamino)phenyl)-H-imidazo[1,2-a]pyridin-6-ol (L12). In a dried 10 mL flask under nitrogen flow, was added the 6-methoxy-imidazopyridine (62 mg, 0.22 mmol) and 2 mL of anhydrous DCM. The stirring solution was cooled at −78° C. with a CO$_2$/acetone bath and BBr$_3$ (80 mg, 0.32 mmol) was added dropwise by a disposable syringe. (Caution! BBr$_3$ reacts violently with water). The reaction mixture was allowed to stir at RT for 2 hrs, and poured into 15 mL ice/water. The mixture of CH$_2$Cl$_2$ and CH$_3$OH (15:1) was added and the mixture stirred for 10 min. The organic phase was separated, dried over MgSO$_4$, and filtered. The solvent was removed to give 39 mg (yield 70%) of the product as yellow solid. M.p.=262-264° C. $^1$H NMR (270 MHz; DMSO-d$_6$), δ 9.70 (s, 1H, OH), 8.16 (s, 1H, H-3), 8.01 (s, 1H, H-5), 7.71 (d, $^3$J$_{HH}$=8.9 Hz, 2H, Ar—H), 7.45 (d, $^3$J$_{HH}$=9.6 Hz, 1H, Ar—H), 7.03 (d, $^3$J$_{HH}$=9.4, 1H, Ar—H), 6.78 (d, $^3$J$_{HH}$=8.9 Hz, 2H, Ar—H), 2.95 (s, 6H, NCH$_3$); $^{13}$C{$^1$H} NMR (125 MHz, DMSO-d$_6$), δ 150.2, 146.2, 143.2, 140.3, 126.4 (Ph-2, 6), 120.7 (C7), 120.4, 115.3 (C8), 112.4 (Ph-3,5), 110.5 (C3), 107.8 (C5), 39.9 (NCH$_3$). m/z (CI-MS): 254 ([M+1]$^+$), 238 ([M−CH$_3$]$^+$).

4-(6-(ethylthio)-H-imidazo[1,2-a]pyridin-2-yl)-N,N-dimethylbenzenamine (T7). 2-Bromo-1-(4-(dimethylamino) phenylethanone (11) (1.21 g; 5.00 mmol) and 5-(ethylthio) pyridin-2-amine (7h) (0.80 g; 5.2 mmol) were used to give 12 h (0.91 g; yield 61%); mp: 168-171° C.; $^1$H NMR (400 MHz, DMSO-d$_6$) δ 8.56 (dd, $^4$J$_{HH}$=1.9 Hz, $^5$J$_{HH}$=0.9 Hz, 1H, Ar—H), 8.14 (s, 1H, Ar—H), 7.78-7.74 (m, 2H, Ar—H), 7.51-7.49 (m, 1H, Ar—H), 7.23 (dd, $^3$J$_{HH}$=9.3 Hz, $^4$J$_{HH}$=1.9 Hz, 1H, Ar—H), 6.76 (m, 2H, Ar—H), 2.94 (s, 6H, CH$_3$), 2.92 (q, $^3$J$_{HH}$=7.3 Hz, 2H, CH$_2$), 1.21 (t, $^3$J$_{HH}$=7.3 Hz, 3H, CH$_3$). $^{13}$C NMR (100 MHz, DMSO-d$_6$) δ 150.1, 145.7, 143.6, 128.0, 127.3, 126.5 (s, 2C, Ar), 121.5, 118.3, 116.1, 112.2 (s, 2C, Ar), 107.1, 40.0 (s, 2C, CH$_3$), 28.4 (s, 1C, CH$_2$), 14.4 (s, 1C, CH$_3$). m/z (ES-MS): 300.1 (6%), 299.1 (39%), 298.1 (100%, [M+H]$^+$). HRMS m/z (TOF$^+$): Calc. C$_{17}$H$_{20}$N$_3$S=298.1378. Found: 298.1386. Error (ppm): +2.7.

4-(6-bromo-8-iodoindolizin-2-yl)-N,N-dimethylbenzenamine (L13). 2-Bromo-1-(4-(dimethylamino)phenylethanone (11) (1.21 g; 5.00 mmol) and 2-amino-3-iodo-5-bromopyridine (7i) (1.58 g; 5.3 mmol) were used to give 12i (1.21 g; yield 55%); mp: 218-220° C.; $^1$H NMR (400 MHz, CDCl$_3$) δ 8.17 (d, $^4$J$_{HH}$=1.7 Hz, 1H, Ar—H), 7.85-7.81 (m, 2H, Ar—H), 7.79 (s, 1H, Ar—H), 7.66 (d, $^4$J$_{HH}$=1.7 Hz, 1H, Ar—H), 6.79 (d, $^3$J$_{HH}$=7.9 Hz, 2H, Ar—H), 2.99 (s, 3H, CH$_3$). $^{13}$C NMR (100 MHz, CDCl$_3$) δ 150.5, 147.9, 143.9, 135.8, 127.5 (s, 2C, Ar), 125.4, 121.5, 112.8 (s, 2C, Ar), 108.8, 106.0, 84.0 (s, 1C, Ar—I), 40.9 (s, 1C, CH$_3$). m/z (ES-MS): 444.9 (6%), 443.9 (99%), 442.9 (9%), 441.9 (100%, [M+H]$^+$). HRMS m/z (TOF$^+$): Calc. C$_{15}$H$_{14}$N$_3$BrI=441.9416. Found: 441.9398. Error (ppm): −4.1.

6-bromo-2-(4-(dimethylamino)phenyl)indolizine-8-carbonitrile (L14). 2-Bromo-1-(4-(dimethylamino)phenyl)ethanone (11) (1.21 g; 5.00 mmol) and 2-amino-5-bromonicotinonitrile (7j) (1.03 g; 5.2 mmol) were used to give 12j (0.77 g; yield 45%); mp: 240-246° C.; $^1$H NMR (400 MHz, DMSO-d$_6$) δ 9.12 (d, $^4$J$_{HH}$=1.8 Hz, 1H, Ar—H), 8.32 (s, 1H, Ar—H), 8.13 (d, $^4$J$_{HH}$=1.8 Hz, 1H, Ar—H), 7.81 (d, $^3$J$_{HH}$=8.9 Hz, 2H, Ar—H), 6.79 (d, $^3$J$_{HH}$=8.9 Hz, 2H, Ar—H), 2.96 (s, 3H, CH$_3$). $^{13}$C NMR (100 MHz, DMSO-d$_6$) δ 150.6, 147.4, 141.3, 133.6, 131.1, 127.0 (s, 2C, Ar), 119.9, 114.8, 112.1 (s, 2C, Ar), 109.0, 103.5, 99.9, 39.9 (s, 2C, NCH$_3$). m/z (ES-MS): 443.9 (4%), 441.9 (3%), 344.0 (11%), 343.0 (98%), 342.0 (11%), 341.0 (100%, [M+H]$^+$). HRMS m/z (TOF$^+$): Calc. C$_{16}$H$_{14}$N$_4$Br=341.04. Found: 341.0389. Error (ppm): −3.8.

N-(2-bromo-4-(6-bromo-H-imidazo[1,2-a]pyridin-2-yl)phenyl)-2,2,2-trifluoro-N-methylacetamide (L15). N-(2-Bromo-4-(2'-bromoacetyl)phenyl)-2,2,2-trifluoro-N-methylacetamide (4a) (4.0 g; 9.93 mmol) and 5-bromopyridin-2-amine (7b) (1.7 g; 9.83 mmol) were dissolved in MeOH (20 mL). The reaction mixture was refluxed for 8 h and solvent then removed. A small amount of CH$_2$Cl$_2$ was added and the resultant precipitate filtered off to afford 13a (2.8 g; yield 59%) as a yellow solid; mp: 95-98° C.; $^1$H NMR (400 MHz, CD$_3$OD) δ Isomer α (84%) 8.73-8.72 (m, 1H, Ar—H), 8.34-8.31 (m, 2H, Ar—H), 8.01 (dd, $^3$J$_{HH}$=8.2 Hz, $^4$J$_{HH}$=2.0 Hz, 1H, Ar—H), 7.58 (d, $^3$J$_{HH}$=8.3 Hz, 1H, Ar—H), 7.55-7.52 (m, 1H, Ar—H), 7.45 (dd, $^3$J$_{HH}$=9.6 Hz, $^4$J$_{HH}$=1.9 Hz, 1H, Ar—H), 2.66 (s, 3H, CH$_3$). Isomer β (16%) 8.73-8.72 (m, 1H, Ar—H), 8.34-8.31 (m, 2H, Ar—H), 8.03 (dd, $^3$J$_{HH}$=8.0 Hz, $^4$J$_{HH}$=1.9 Hz, 1H, Ar—H), 7.55-7.52 (m, 1H, Ar—H), 7.51 (d, $^3$J$_{HH}$=8.3 Hz, 1H, Ar—H), 7.44 (dd, $^3$J$_{HH}$=9.6 Hz, $^4$J$_{HH}$=1.9 Hz, 1H, Ar—H), 2.66 (s, 3H, CH$_3$). $^{13}$C NMR (100 MHz, DMSO-d$_6$) δ Isomer α 155.5 (q, $^2$J$_{CF}$=35.1 Hz, 1C, CO), 143.5, 142.3, 137.9, 136.3, 130.8, 129.8, 128.6, 125.8, 122.8, 117.9, 115.9 (q, $^1$J$_{CF}$=286 Hz, 1C, CF$_3$), 111.1, 106.5, 37.7 (s, 1C, CH$_3$). Isomer β 155.5 (q, $^2$J$_{CF}$=35.1 Hz, 1C, CO), 143.4, 142.6, 139.8, 135.6, 129.9, 129.4, 128.4, 127.1, 126.3, 121.3, 117.8, 115.9 (q, $^1$J$_{CF}$=286 Hz, 1C, CF$_3$), 110.8, 109.4, 37.7 (s, 1C, CH$_3$). m/z (ES-MS): 479.9 (27%), 477.9 (100%, [M+H]$^+$), 475.9 (28%). HRMS m/z (TOF$^+$): Calc. C$_{16}$H$_{11}$N$_3$OF$_3$Br$_2$=475.9221. Found: 475.9228. Error (ppm): +1.5.

N-(4-(6-bromoindolizin-2-yl)-2-methylphenyl)-N-methylacetamide (L16). N-(4-(2'-Bromoacetyl)-2-methylphenyl)-N-methylacetamide (4c) (1.0 g; 3.52 mmol) and 5-bromopyridin-2-amine (7b) (0.73 g; 4.22 mmol) were used. Yield 37%. M.p. 197-198° C.; $^1$H NMR (400 MHz, DMSO-d$_6$) δ Isomer α (90%) 8.88 (dd, $^4$J$_{HH}$=2.0 Hz, $^5$J$_{HH}$=0.8 Hz, 1H, Ar—H), 8.39 (d, $^5$J$_{HH}$=0.4 Hz, 1H, Ar—H), 7.89 (dd, $^3$J$_{HH}$=7.8 Hz, $^4$J$_{HH}$=1.8 Hz, 1H. Ar—H), 7.84 (d, $^4$J$_{HH}$=1.8 Hz, 1H. Ar—H), 7.58-7.54 (m, 1H, Ar—H), 7.43 (d, $^3$J$_{HH}$=8.0 Hz, 1H, Ar—H), 7.37 (dd, $^3$J$_{HH}$=9.5 Hz, $^4$J$_{HH}$=2.0 Hz, 1H. Ar—H), 3.11 (s, 3H, NCH$_3$), 2.21 (s, 3H, Ar—CH$_3$), 1.70 (s, 3H, CH$_3$). Isomer β (10%) 8.87 (dd, $^4$J$_{HH}$=1.9 Hz, $^5$J$_{HH}$=0.8 Hz, 1H, Ar—H), 8.32 (d, $^5$J$_{HH}$=0.3 Hz, 1H, Ar—H), 7.76 (dd, $^3$J$_{HH}$=7.8 Hz, $^4$J$_{HH}$=1.8 Hz, 1H, Ar—H), 7.73 (d, $^4$J$_{HH}$=1.8 Hz, 1H, Ar—H), 7.56-7.53 (m, 1H, Ar—H), 7.36 (dd, $^3$J$_{HH}$=9.5 Hz, $^4$J$_{HH}$=2.0 Hz, 1H. Ar—H), 7.31 (d, $^3$J$_{HH}$=8.0 Hz, 1H, Ar—H), 3.28 (s, 3H, NCH$_3$), 2.13 (s, 3H, Ar—CH$_3$), 1.70 (s, 3H, CH$_3$). $^{13}$C NMR (100 MHz, DMSO-d$_6$) δ Isomer α 169.0 (s, 1C, CO), 144.2, 143.3, 143.2, 134.7, 133.0, 131.7, 127.9, 126.9, 125.3, 125.1, 117.6, 109.8, 106.0, 35.3 (s, 1C, NCH$_3$), 21.6 (s, 1C, CH$_3$), 16.7 (s, 1C, Ar—CH$_3$). Isomer β 169.6 (s, 1C, CO), 144.6, 143.8, 143.2, 134.8, 132.2, 130.9, 127.8, 126.8, 124.5, 124.1, 117.5, 109.3, 105.9, 38.7 (s, 1C, NCH$_3$), 21.9 (s, 1C, CH$_3$), 17.1 (s, 1C, Ar—CH$_3$). m/z (ES-MS): 361.0 (4%), 360.0 (100%, [M+H]$^+$), 359.0 (47%), 358.0 (96%). HRMS m/z (TOF$^+$): Calc. C$_{17}$H$_{17}$N$_3$OBr=358.0555. Found: 358.0557. Error (ppm): +0.6.

N-(4-(6-bromoindolizin-2-yl)-2-methylphenyl)-2,2,2-trifluoroacetamide (L17). N-(4-(2-bromoacetyl)-2-methylphenyl)-2,2,2-trifluoroacetamide (3.0 g; 9.26 mmol) and 5-bromopyridin-2-amine (1.5 g; 8.67 mmol) were dissolved in 20 mL ethanol. The mixture was refluxed overnight, and the solvent was removed. CH$_2$Cl$_2$ was added to precipitate a solid, which was filtered and washed with CH$_2$Cl$_2$, to afford 1.0 g (yield 28%) of product as a yellow powder. $^1$H NMR (300 MHz; DMSO-d$_6$), δ 11.1 (s, 1H, NH), 9.14 (s, 1H, Ar—H), 8.60 (s, 1H, Ar—H), 7.90-7.76 (m, 4H, Ar—H), 7.46 (d, $^3$J$_{HH}$=8.0 Hz, 1H, Ar—H), 2.19 (s, 3H, Ar—CH$_3$).

2-bromo-4-(6-bromo-H-imidazo[1,2-a]pyridin-2-yl)-N-methylbenzenamine (L18). N-(2-bromo-4-(6-bromo-H-imidazo[1,2-a]pyridin-2-yl)phenyl)-2,2,2-trifluoro-N-methylacetamide (1.0 g; 2.10 mmol) and K$_2$CO$_3$ (2.0 g; 14.5 mmol) were suspended in 30 mL ethanol and 15 mL water. The mixture was refluxed over 8 hrs. The organic solvent was removed, and CH$_2$Cl$_2$ was added. The organic phase was washed with H$_2$O twice, and dried over MgSO$_4$. The solvent was removed to afford 0.60 g (yield 80%) of product as a yellow solid. $^1$H NMR (300 MHz; DMSO-d$_6$), δ 8.80 (s, 1H, Ar—H), 8.20 (s, 1H, Ar—H), 7.98 (d, $^4$J$_{HH}$=1.8 Hz, 1H, Ar—H), 7.76 (dd, $^3$J$_{HH}$=8.5 Hz, $^4$J$_{HH}$=1.8 Hz, 1H, Ar—H), 7.49 (d, $^3$J$_{HH}$=9.5 Hz, 1H, Ar—H), 7.30 (dd, $^3$J$_{HH}$=9.4 Hz, $^4$J$_{HH}$=1.7 Hz, 1H, Ar—H), 6.67 (d, $^3$J$_{HH}$=8.5 Hz, 1H, Ar—H), 2.78 (s, 3H, CH$_3$).

4-(6-bromo-H-imidazo[1,2-a]pyridin-2-yl)-N,2-dimethylbenzenamine (L19). N-(4-(6-Bromoimidazo[1,2-a]pyridin-2-yl)-2-methylphenyl)-N-methylacetamide (13c, 1.0 g; 2.79 mmol) and KOH (1.0 g; 17.8 mmol) were used, to afford 0.68 g. Yield 77%. M.p. 165-166° C.; $^1$H NMR (400 MHz, DMSO-d$_6$) δ 8.82 (dd, $^4$J$_{HH}$=1.8 Hz, $^5$J$_{HH}$=0.7 Hz, 1H, Ar—H), 8.27 (s, 1H, Ar—H), 7.56 (d, $^3$J$_{HH}$=9.5 Hz, 1H, Ar—H), 7.33 (dd, $^3$J$_{HH}$=9.5 Hz, $^4$J$_{HH}$=1.9 Hz, 1H, Ar—H), 7.10-7.09 (m, 2H, Ar—H), 7.01 (dd, $^3$J$_{HH}$=8.3 Hz, $^5$J$_{HH}$=0.3 Hz, 1H, Ar—H), 5.12 (s, 1H, N—H), 2.82 (s, 1H, CH$_3$), 2.10 (s, 1H, CH$_3$). $^{13}$C NMR (100 MHz, DMSO-d$_6$) δ 147.8, 146.4, 143.1, 131.9, 129.8, 127.3, 126.6, 121.8, 117.5, 113.2, 108.9, 105.7, 105.6, 30.2 (s, 1C, N—CH$_3$), 17.5 (s, 1C, Ar—CH$_3$). m/z (ES-MS): 319.0 (17%), 318.0 (96%), 317.0 (22%), 316.0 (100%, [M+H]$^+$). HRMS m/z (TOF$^+$): Calc. C$_{15}$H$_{15}$N$_3$Br=316.0449. Found: 316.0453. Error (ppm): +1.3.

4-(6-bromo-H-imidazo[1,2-a]pyridin-2-yl)-2-methylbenzenamine (L20). N-(4-(6-bromo-H-imidazo[1,2-a]pyridin-2-yl)-2-methylphenyl)-2,2,2-trifluoroacetamide (1.0 g; 2.51 mmol) and K$_2$CO$_3$ (4.0 g; 29.0 mmol) were suspended in 30 mL ethanol and 15 mL water. The mixture was refluxed overnight. The solvent was removed, and CH$_2$Cl$_2$ was added. The organic phase was washed with H$_2$O twice, and dried over MgSO$_4$. The solvent was removed to afford a solid which was purified by silica gel column chromatography to obtain 0.60 g (yield 79%) of product as yellow solid. $^1$HNMR (300 MHz; DMSO-d$_6$), δ 8.81 (s, 1H, Ar—H), 8.13 (s, 1H, Ar—H), 7.49 (d, $^3$J$_{HH}$=9.5 Hz, 1H, Ar—H), 7.30 (d, $^3$J$_{HH}$=9.5

Hz, 1H, Ar—H), 7.25 (s, 1H, Ar—H), 7.03 (d, $^3J_{HH}$=7.4 Hz, 1H, Ar—H), 6.95 (d, $^3J_{HH}$=7.7 Hz, 1H, Ar—H), 2.06 (s, 3H, Ar—CH$_3$).

4-(6-chloroimidazo[1,2-a]pyrazin-2-yl)-N,N-dimethylbenzenamine (L21). In a double necked round bottomed flask equipped with condenser and under nitrogen flow were introduced 5-chloro-2-amino-pyrazine (61 mg, 0.47 mmol), 2-bromo-4'-dimethylamino-acetophenone (170 mg, 0.71 mmol) and anhydrous acetonitrile (7 mL). The reaction mixture was refluxed for 3 hrs. After it cooled down, NaHCO$_3$ (71 mg, 0.85 mmol) was added. The reaction was refluxed for another 6 hrs. The solvent was removed and the crude product (221 mg) was purified by FCC (hex/DCM/AcOEt=2:2:1), to afford 9 mg (yield 7%) of the product as yellow solid. $^1$HNMR (270 MHz; CDCl$_3$), δ 8.82 (s, 1H, Ar—H), 8.09 (s, 1H, Ar—H), 7.822 (s, 1H, Ar—H), 7.818 (d, $^3J_{HH}$=8.9 Hz, 2H, Ar—H), 6.77 (d, $^3J_{HH}$=8.7 Hz, 2H, Ar—H), 3.02 (s, 6H, NCH$_3$). m/z (CI-MS): 273 ([M+1]$^+$), 261, 239 ([M−Cl+1]$^+$).

4-(6-chloroimidazo[1,2-a]pyrimidin-2-yl)-N,N-dimethylbenzenamine (L22). 2-Amino-5-chloro-pyrimidine (0.150 g, 1.16 mmol), 2-bromo-4'-dimethylamino-acetophenone (0.56 g, 2.32 mmol) and 16 mL of anhydrous acetonitrile were added to a double-neck flask equipped with a condenser under dinitrogen. A small amount of anhydrous DMF (0.5 mL) was added to completely dissolve the amine. After 3 hrs of stirring and refluxing, the mixture was cooled down and NaHCO$_3$ (0.19 g, 2.32 mmol) was added. The reaction mixture was refluxed for another 6 hrs and was filtered hot on a Busch funnel to collect the precipitate, which was washed with portions of EtOH, water, EtOH, and dried overnight, to afford 72 mg (yield 23%) of the product as yellow powder. M.p.=256-258° C. $^1$H NMR (270 MHz; CDCl$_3$), δ 8.37 (d, 2H, $^4J_{HH}$=2.7 Hz, Ar—H), 7.88 (d, $^3J_{HH}$=9.2 Hz, 2H, Ar—H), 7.67 (s, 1H, H-3), 6.79 (d, $^3J_{HH}$=8.7, 2H, Ar—H), 3.01 (s, 6H, NCH$_3$). $^{13}$C{$^1$H} NMR (125 MHz, $^{13}$C, CDCl$_3$), δ 150.5, 149.3, 147.9 (C7), 147.0, 129.6 (C5), 127.5 (Ph-2,6), 117.5, 112.8 (Ph-3,5), 106.2 (C—Cl), 104.8 (C3), 40.7 (NCH$_3$). m/z (CI-MS): 273 ([M+1]$^+$), 239 ([M−Cl+1]$^+$). Calc. C$_{14}$H$_{13}$ClN$_4$: C, 61.75; H, 4.82; N, 20.59. Found: C, 58.32; H, 4.88; N, 18.81.

General procedure for thiolate substitution: A 10 mL microwave tube was charged with Pd$_2$dba$_3$ (13-58 mg, 0.014-0.063 mmol, 10-20 mol % Pd), DiPPF (6-27 mg, 0.014-0.063 mmol, 10-20 mol %), IMPY derivative (0.14-0.32 mmol), and tin-thiolate (0.29-0.63 mmol). The tube was capped, and put in a microwave system for desired temperature and time as specified in the text. A small sample of the resulting suspension was analyzed by HPLC to confirm the conversion. The suspension was partitioned between CHCl$_3$ and K$_2$CO$_3$ solution. The organic layer was dried over MgSO$_4$ and filtered. The solvent was removed, and the residue was dissolved in DMSO, and loaded on a reversed phase HPLC. After proper band was collected, the solvents were removed, and the product was dried by azetrope with CH$_3$CN to provide the desired product.

2-(2-(4-(methylamino)phenyl)-H-imidazo[1,2-a]pyridin-6-ylthio)acetamide (T1). 4-(6-Iodo-H-imidazo[1,2-c]pyridin-2-yl)-N-methylbenzenamine (100 mg, 0.29 mmol), N-methyl-N-(trimethylstannyl)methanamine (60 mg, 0.29 mmol), 2-mercaptoacetamide (26 mg, 0.29 mmol), Pd$_2$(dba)$_3$ (26.2 mg, 0.029 mmol), DiPPF (12 mg, 0.029 mmol), and 8.0 mL of toluene were used.

Mp: 198-202° C.; $^1$H NMR (400 MHz, DMSO-d$_6$) δ 8.68 (d, $^4J_{HH}$=4.4 Hz, 1H, Ar—H), H), 8.11 (s, 1H, Ar—H), 7.68 (d, $^3J_{HH}$=8.0 Hz, 2H, Ar—H), 7.48 (d, $^3J_{HH}$=9.6 Hz, 1H, Ar—H), 7.26 (d, $^3J_{HH}$=9.2 Hz, 1H, Ar—H), 7.13 (s, 1H, Ar—H), 6.59 (d, $^3J_{HH}$=8.0 Hz, 2H, Ar—H), 5.86 (s, 2H, NH$_2$), 3.53 (s, 2H, CH$_2$S), 2.71 (s, 3H, CH$_3$). $^{13}$C{$^1$H} NMR (400 MHz, DMSO-d$_6$) δ 169.8 (—CO—N), 149.8, 146.2, 143.6, 128.0, 127.7, 126.6, 120.9, 118.2, 115.9, 111.6, 106.8, 38.5 (C—S), 29.6 (NCH$_3$). m/z (LC-MS): 314.3 (21%), 313.2 (100%, [M+H]$^+$), 255.5 (32%, [M–CH$_2$CONH$_2$]$^+$). HRMS m/z (TOF$^+$): Calc. C$_{16}$H$_{17}$N$_4$OS=313.1123. Found: 313.1126. Error (ppm): +0.9.

2-(2-(4-(dimethylamino)phenyl)-H-imidazo[1,2-a]pyridin-6-ylthio)acetamide (T2). 4-(6-Iodo-H-imidazo[1,2-a]pyridin-2-yl)-N,N-dimethylbenzenamine (50 mg, 0.14 mmol), N-methyl-N-(trimethylstannyl)methanamine (30 mg, 0.14 mmol), 2-mercaptoacetamide (13 mg, 0.14 mmol), Pd$_2$(dba)$_3$ (13 mg, 0.014 mmol), DiPPF (6 mg, 0.014 mmol), and 5.0 mL of toluene were used.

Mp: 180-183° C.; $^1$H NMR (400 MHz, DMSO-d$_6$) δ 8.60 (s, 1H, Ar—H), 8.17 (s, 1H, Ar—H), 7.77 (d, $^3J_{HH}$=8.8 Hz, 2H, Ar—H), 7.50 (d, $^3J_{HH}$=7.9 Hz, 1H, Ar—H), 7.27 (d, $^3J_{HH}$=9.4 Hz, 1H, Ar—H), 7.13 (brs, 2H, NH$_2$), 6.78 (d, $^3J_{HH}$=8.7 Hz, 2H, Ar—H), 3.54 (s, 2H, CH$_2$S), 2.94 (s, 6H, N(CH$_3$)$_2$). $^{13}$C{$^1$H} NMR (400 MHz, DMSO-d$_6$) δ 168.7 (—CO—N), 149.0, 144.7, 142.5, 129.4, 127.8, 126.9, 126.6, 125.3, 120.3, 117.2, 114.9, 111.1, 109.5, 106.1, 38.5 (C—S), 37.3 (NCH$_3$). m/z (LC-MS): 329.3 (7%), 328.2 (18%), 327.2 (100%, [M+H]$^+$), 325.1 (12%), 323.4 (7%), 321.7 (7%), 320.9 (5%), 269.4 (14%, [M–CH$_2$CONH$_2$]$^+$). HRMS m/z (TOF$^+$): Calc. C$_{17}$H$_{19}$N$_4$OS=327.1280. Found: 327.1278. Error (ppm): −0.5.

2-(2-(4-(methylamino)phenyl)-H-imidazo[1,2-a]pyridin-6-ylthio)ethanol (T3). 4-(6-Iodo-H-imidazo[1,2-a]pyridin-2-yl)-N-methylbenzenamine (100 mg, 0.29 mmol), N-methyl-N-(trimethylstannyl)methanamine (60 mg, 0.29 mmol), 2-mercaptoethanol (23 mg, 0.29 mmol), Pd$_2$(dba)$_3$ (28 mg, 0.031 mmol), DiPPF (22 mg, 0.039 mmol), and 5.0 mL of toluene were used.

Mp: 158-161° C.; $^1$H NMR (400 MHz, CD$_3$OD) δ 8.51 (s, 1H, Ar—H), 7.95 (s, 1H, Ar—H), 7.68 (d, $^3J_{HH}$=8.6 Hz, 2H, Ar—H), 7.45 (d, $^3J_{HH}$=8.6 Hz, 1H, Ar—H), 7.34 (d, $^3J_{HH}$=8.6 Hz, 1H, Ar—H), 6.67 (d, $^3J_{HH}$=8.6 Hz, 2H, Ar—H), 3.69 (t, $^3J_{HH}$=6.5 Hz, 2H, OCH$_2$), 3.01 (t, $^3J_{HH}$=6.5 Hz, 2H, SCH$_2$), 2.81 (s, 3H, NCH$_3$). $^{13}$C{$^1$H} NMR (400 MHz, CD$_3$OD) δ 151.8, 148.0, 145.7, 130.9, 129.5, 128.1, 122.6, 121.2, 116.5, 113.4, 108.5, 61.5 (C—O), 38.8 (C—S), 30.6 (NCH$_3$). m/z (LC-MS): 302.2 (5%), 301.3 (15%), 300.2 (100%, [M+H]$^+$). HRMS m/z (TOF$^+$): Calc. C$_{16}$H$_{18}$N$_3$OS=300.1171. Found: 300.1163. Error (ppm): −2.5.

2-(2-(4-(dimethylamino)phenyl)-H-imidazo[1,2-a]pyridin-6-ylthio)ethanol (T4). 4-(6-Iodo-H-imidazo[1,2-a]pyridin-2-yl)-N,N-dimethylbenzenamine (50 mg, 0.14 mmol), N-methyl-N-(trimethylstannyl)methanamine (29 mg, 0.14 mmol), 2-mercaptoethanol (11 mg, 0.14 mmol), Pd$_2$(dba)$_3$ (13 mg, 0.014 mmol), DiPPF (6 mg, 0.014 mmol), and 5.0 mL of toluene were used.

Mp: 183-185° C.; $^1$H NMR (400 MHz, CD$_3$OD) δ 8.50 (s, 1H, Ar—H), 8.05 (s, 1H, Ar—H), 7.78 (d, $^3J_{HH}$=8.9 Hz, 2H, Ar—H), 7.45 (d, $^3J_{HH}$=8.9 Hz, 1H, Ar—H), 7.35 (d, $^3J_{HH}$=8.9 Hz, 1H, Ar—H), 6.83 (d, $^3J_{HH}$=8.9 Hz, 2H, Ar—H), 3.70 (t, $^3J_{HH}$=6.7 Hz, 2H, OCH$_2$), 3.03 (t, $^3J_{HH}$=6.7 Hz, 2H, SCH$_2$), 3.00 (s, 6H, NCH$_3$). $^{13}$C{$^1$H} NMR (400 MHz, DMSO-d$_6$) δ 150.1, 145.7, 143.6, 128.1, 127.4, 126.4, 121.5, 118.5, 116.1, 112.2, 107.1, 59.8 (C—O), 55.9 (C—S), 37.2 (NCH$_3$). m/z (LC-MS): 316.1 (5%), 315.2 (23%), 314.2 (100%, [M+H]$^+$). HRMS m/z (TOF$^+$): Calc. C$_{17}$H$_{20}$N$_3$OS=314.1327. Found: 314.1317. Error (ppm): −3.4.

4-(6-(4-methoxybenzylthio)-H-imidazo[1,2-a]pyridin-2-yl)-N,N-dimethylbenzenamine (T5). 4-(6-Iodo-H-imidazo[1,2-c]pyridin-2-yl)-N,N-dimethylbenzenamine (80 mg, 0.22 mmol), N-methyl-N-(trimethylstannyl)methanamine (46 mg, 0.22 mmol), (4-methoxyphenyl)methanethiol (34 mg, 0.22 mmol), $Pd_2(dba)_3$ (40 mg, 0.044 mmol), DiPPF (18.4 mg, 0.044 mmol), and 5.0 mL of toluene were used.

Mp: 184-186° C.; $^1H$ NMR (400 MHz, $CD_3OD$) δ 8.43 (s, 1H, Ar—H), 8.10 (s, 1H, Ar—H), 7.75 (d, $^3J_{HH}$=8.4 Hz, 2H, Ar—H), 7.47 (d, $^3J_{HH}$=8.0 Hz, 1H, Ar—H), 7.19 (d, $^3J_{HH}$=8.0 Hz, 1H, Ar—H), 7.16 (d, $^3J_{HH}$=8.0 Hz, 2H, Ar—H), 6.83 (d, $^3J_{HH}$=8.0 Hz, 1H, Ar—H), 6.77 (d, $^3J_{HH}$=8.0 Hz, 1H, Ar—H), 4.13 (s, 2H, $CH_2S$), 3.71 (s, 3H, $CH_3O$), 2.94 (s, 6H, $NCH_3$). $^{13}C\{^1H\}$ NMR (400 MHz, DMSO-$d_6$) δ 158.2, 150.0, 145.6, 143.5, 129.9, 129.2, 128.2, 127.7, 126.3, 121.3, 118.0, 115.8, 113.9, 112.1, 107.0, 54.8 ($OCH_3$), 39.9 ($NCH_3$), 38.3 (C—S). m/z (LC-MS): 392.1 (7%), 391.1 (23%), 390.1 (100%, [M+H]$^+$). HRMS m/z (TOF$^+$): Calc. $C_{23}H_{24}N_3OS$=390.1640. Found: 390.1634. Error (ppm): −0.6.

N,N-dimethyl-4-(6-(methylthio)-H-imidazo[1,2-a]pyridin-2-yl)benzenamine (T6). 4-(6-Iodo-H-imidazo[1,2-a]pyridin-2-yl)-N,N-dimethylbenzenamine (90 mg, 0.25 mmol), 1,2-dimethyldisulfane (28 mg, 0.30 mmol), 1,1,1,2,2,2-hexamethyldistannane (97 mg, 0.30 mmol), $Pd_2(dba)_3$ (22.8 mg, 0.025 mmol), DiPPF (10.5 mg, 0.025 mmol), and 4.0 mL of toluene were used.

Mp: 155-164° C.; $^1H$ NMR (400 MHz, $CD_3OD$) 6 8.34 (s, 1H, Ar—H), 7.96 (s, 1H, Ar—H), 7.73 (d, $^3J_{HH}$=9.4 Hz, 2H, Ar—H), 7.44 (d, $^3J_{HH}$=9.4 Hz, 1H, Ar—H), 7.26 (dd, $^3J_{HH}$=9.4 Hz, $^4J_{HH}$=2.2 Hz, 1H, Ar—H), 6.82 (d, $^3J_{HH}$=8.9 Hz, 2H, Ar—H). $^{13}C\{^1H\}$ NMR (400 MHz, $CD_3OD$) δ 152.3, 147.6, 145.6, 129.0, 128.1, 125.9, 124.6, 122.8, 116.7, 113.9, 108.8, 40.9 (C—S), 17.9 ($NCH_3$). m/z (LC-MS): 286.2 (4%), 285.3 (13%), 284.2 (100%, [M+H]$^+$). HRMS m/z (TOF$^+$): Calc. $C_{16}H_{18}N_3S$=284.1221. Found: 284.1215. Error (ppm): −2.4.

2-(2-(3-methyl-4-(methylamino)phenyl)-H-imidazo[1,2-a]pyridin-6-ylthio)acetamide (T8). 4-(6-Bromo-H-imidazo[1,2-a]pyridin-2-yl)-N,2-dimethylbenzenamine (100 mg, 0.32 mmol), N-methyl-N-(trimethylstannyl)methanamine (99 mg, 0.48 mmol), 2-mercaptoacetamide (43 mg, 0.48 mmol), $Pd_2(dba)_3$ (43 mg, 0.048 mmol), DiPPF (20 mg, 0.048 mmol), and 6.0 mL of toluene were used.

Mp: 181-182° C.; $^1H$ NMR (400 MHz, $CD_3OD$) δ 8.58 (s, 1H, Ar—H), 8.10 (s, 1H, Ar—H), 7.49 (d, $^3J_{HH}$=8.0 Hz, 1H, Ar—H), 7.41 (d, $^3J_{HH}$=8.0 Hz, 1H, Ar—H), 7.17 (s, 1H, Ar—H), 7.12 (d, $^3J_{HH}$=8.0 Hz, 1H, Ar—H), 7.06 (d, $^3J_{HH}$=8.0 Hz, 1H, Ar—H), 6.54 (s, 1H, NH), 3.55 (s, 2H, $SCH_2$), 2.93 (s, 3H, $NCH_3$), 2.16 (s, 3H, Ar—$CH_3$). $^{13}C\{^1H\}$ NMR (400 MHz, DMSO-$d_6$) δ 168.7 (—CO—), 146.6, 144.9, 142.4, 131.0, 128.6, 127.1, 126.6, 120.5, 117.5, 115.3, 112.0, 107.5, 104.5, 37.2 ($CH_2S$), 29.0 ($NCH_3$), 16.3 ($CH_3$). m/z (LC-MS): 329.2 (6%), 328.3 (22%), 327.2 (100%, [M+H]$^+$). HRMS m/z (TOF$^+$): Calc. $C_{17}H_{19}N_4OS$=327.1280. Found: 327.1278. Error (ppm): −0.4.

2-(2-(3-methyl-4-(methylamino)phenyl)-H-imidazo[1,2-a]pyridin-6-ylthio)ethanol (T9). 4-(6-Bromo-H-imidazo[1,2-a]pyridin-2-yl)-N,2-dimethylbenzenamine (100 mg, 0.32 mmol), N-methyl-N-(trimethylstannyl)methanamine (132 mg, 0.63 mmol), 2-mercaptoethanol (50 mg, 0.63 mmol), $Pd_2(dba)_3$ (58 mg, 0.063 mmol), DiPPF (27 mg, 0.063 mmol), and 6.0 mL of toluene were used.

Mp: 149-153° C.; $^1H$ NMR (400 MHz, $CD_3OD$) δ 8.55 (s, 1H, Ar—H), 8.10 (s, 1H, Ar—H), 7.50 (d, $^3J_{HH}$=8.0 Hz, 1H, Ar—H), 7.38 (d, $^3J_{HH}$=8.0 Hz, 1H, Ar—H), 7.18 (s, 1H, Ar—H), 7.15 (d, $^3J_{HH}$=8.0 Hz, 1H, Ar—H), 7.08 (d, $^3J_{HH}$=8.0 Hz, 1H, Ar—H), 3.80 (t, $^3J_{HH}$=7.2 Hz, 2H, $CH_2O$), 3.03 (t, $^3J_{HH}$=7.2 Hz, 2H, $CH_2S$), 2.94 (s, 3H, $NCH_3$), 2.16 (s, 3H, Ar—$CH_3$). $^{13}C\{^1H\}$ NMR (400 MHz, DMSO-$d_6$) δ 147.7, 146.0, 143.4, 132.2, 129.7, 128.2, 127.4, 121.6, 118.8, 116.5, 113.1, 108.6, 105.6, 59.5 ($OCH_2$), 37.1 ($CH_2S$), 30.1 ($NCH_3$), 17.5 ($CH_3$). m/z (LC-MS): 329.2 (6%), 328.3 (22%), 327.2 (100%, [M+H]$^+$). m/z (LC-MS): 316.2 (8%), 315.2 (24%), 314.2 (100%, [M+H]$^+$). HRMS m/z (TOF$^+$): Calc. $C_{17}H_{20}N_3OS$=314.1327. Found: 314.1316. Error (ppm): −3.5.

Isolation of human AD amyloid. Postmortem brain tissues were obtained from a confirmed AD patient at the age of 80. Pre- and postmortem consent was obtained from next of kin, and brains were removed at autopsy, sectioned and frozen at −70° C. Bags of brain tissue were removed from the freezer to a −20° C. freezer one day before, and then placed on ice 3 h before the experiment. While working on ice, the brain tissue was cut into small sections, and meninges from outer layer of cortex and from fissures between the lobes of the gray matter was removed. After removing the white matter, the grey matter were chopped into small pieces and placed into plastic bags. The tissue was stored in −70° C. freezer for further use.

In a typical isolation, 60 g of brain tissue were used. Initially, an equal volume of 1% SDS was added to homogenize. More 1% SDS was added later until 200 mL. The mixture was vortexed, distributed evenly among 10 Beckman ultracentrifuge tubes, and centrifuged by a Coulter type 55.2 Ti ultracentrifuge rotor using RPM: 40,000; G force: 180,000; temp: 4° C.; time: 30 min. The collected bottom pellets were further homogenized and centrifuged twice more as described above using 50 mL and 20 mL of 1% SDS each, and finally in 20 mL 1.2 M sucrose. The supernatant along the top pellet was discarded. The pellets at the bottom were homogenized and centrifuged in 20 mL 1.9 M sucrose. The top pellets were collected using a cell scrapper, and the bottom pellets were discarded. The collected top pellets were homogenized and centrifuged using 20 mL deionized water. The bottom pellets were further homogenized and centrifuged using 1.3 M sucrose solution into one centrifuge tube. The bottom pellets were homogenized and centrifuged using 20 mL deionized water. The collected pellets were homogenized in 30 mL of 50 mM Tris-HCl, pH 8.0, 2 mM $CaCl_2$. Collagenase CLS3 (120 mg) and DNAase I (10-15 mg) were added. The mixture was vortexed and incubated for 24-56 hrs at 37° C. in a water bath with shaking. After incubation, the suspension was filtered through 41 μm Millipore filter paper. The collected filtrate was centrifuged and the bottom pellets were homogenized and centrifuged one more time using the Tris-HCl solution. The supernatant was discarded, and the pellets were homogenized and centrifuged using 10 mL 1.9 M sucrose. The top pellet and the 1.9M sucrose layer were transferred to a new tube (this is to remove heavy particles such as metals and salts). Deionized water (40 mL) was added. After homogenization and centrifugation, the collected pellets were put into 500 μL of deionized water to form a homogeneous suspension. It was stored in a refrigerator or freezer for further use.

In Vitro Binding Assay

The amyloid suspension prepared above was diluted by a factor of 40,000 to 50,000 in PBS, and 800 μL suspension was used in each tube. [$^3H$]6-OH-BTA-1 with a concentration of 1 mCi/mL stock solution was diluted using ethanol to give an intermediate solution of 1 μCi/100 μL, which was further diluted using PBS to result in a dilute stock solution of 2.7× $10^{-2}$ μCi/100 μL, and 100 μL, was used in each tube (2 vials with 100 μL of [$^3H$]6-OH-BTA-1 each and scintillation fluid as references). Cold 6-OH-BTA-1 or other displacer was dissolved in ethanol to result in a stock solution of $1 \times 10^{-3}$ M, which was further diluted using PBS or ethanol to result in solutions with concentrations ranging from $1 \times 10^{-5}$ to $10^{-10}$ M, and 100 μL was used in each tube. After assembly, the tubes were vortexed, and incubated for 3 hrs at room temperature. After separation using a cell harvester, the filter paper (GF/B filter paper pretreated with 0.5% polyimine solution) was washed with 10% ethanol in PBS (3×3 mL). The filters were placed into 20 mL glass vials and 10 mL scintillation fluid each was added. After overnight incubation, the samples were counted. The data were analyzed using Graph-Pad Prism 4 or KaleidaGraph 3.6.

Results and Discussion.

Chemical Synthesis

Synthesis of Bromoketones. The nucleus of imidazo[1,2-a]pyridines is made through the condensation between a 2-amino pyridine and an α-haloketone in a manner described before.[2] The reaction tolerates a variety of substituents, including amide and imine groups in both substrates. Two strategies have been developed to synthesize the α-bromoketones (FIG. 1). One is from bromination of ketones. Monomethylation of the amino group of 1-(4-aminophenyl)ethanone follows the method established, to give 1-(4-methylaminophenyl)ethanone, K1.[2] Ortho-bromination of the aromatic amine was accomplished using NBS, a mild bromination agent for activated phenyl group, to give K2 and K3.[3] The amino group was protected using either trifluoroacetyl or acetyl group to give K5 and K6 before bromination of the α-methyl ketone. Three bromination procedures have been reported.[4] One is through tetra-n-butyl ammonium tribromide, the second is through copper (II) bromide, and the third is through the reduction of di-bromides, to afford α-bromoketones B2, B3, B4, B5. The other method to synthesize the α-bromoketones is through Friedel-Crafts reaction to introduce α-bromoacetyl group directly in the aromatic nucleus. The aromatic amino group in A1 and A2 were protected using trifluoroacetyl or acetyl group, to give A3 and A4. Friedel-Crafts reactions using trifluoroacetyl or bromoacetyl bromide catalyzed by $AlCl_3$ in $CS_2$ went smoothly to give B2, B3, B4, B5.[5-7]

Synthesis of 2-Aminopyridines and 2-Aminopyrazines. The synthetic methods of pyridine derivatives depend on the substituents on the ring (FIG. 2). For CN group, halide substitution using CuCN is an optimal choice, such as the synthesis of P3[8-10] and P4 (available from Acros). Some halo group could be introduced through electrophilic substitution of either bromination or iodination, such as the synthesis of P10, P11 and P12.

Substitution of halide by $OCH_3$ and SEt group is more challenging. The first attempts to prepare P5 by a nucleophilic aromatic displacement of the bromide with a methoxy group catalyzed by Cu powder in a conventional way[11] or with microwave heating or an ultrasound bath were frustrated by the apparent unreactivity of the substrate. An attempt was carried out with an ultrasound high power probe (Branson 450 Sonifier) beaming the 40 dB sound waves directly in the solution, but even this technology did not enable the expected transformation (eq 1).

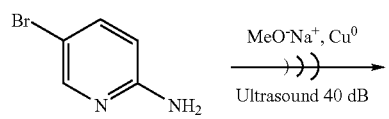

eq1

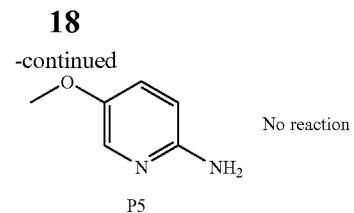

P5  No reaction

Another literature procedure to perform aromatic substitutions with the methoxy anion was followed.[12] The method uses salts of copper (I) and a small amount of ester to form a stabilized tetrahedral adduct which should act as a powerful methoxide donor (FIG. 3). Unfortunately, due to the presence of the free amino group on the bromopyridine and the ethyl acetate as co-catalyst, the reaction product was just the acetamide of the substrate (eq 2).

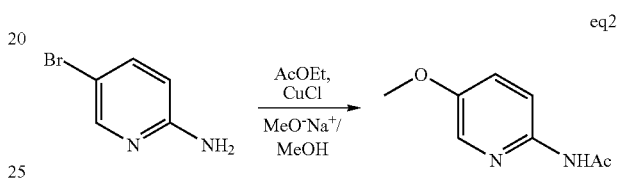

eq2

Attempts to improve the result were made by increasing the equivalents of catalyst used. It was believed that copper could be coordinated and thus inactivated by the nitrogen atoms of the substrate. By this means the expected product was achieved in 36% yield (eq 3). The reaction mixture, after being heated for 14 hrs, still contained a significant amount of starting material together with black polymers. The reaction was quenched to avoid further formation of polymers and degradation of the formed product. In order to decrease the reaction time, the transformation in eq 3 was carried out with microwave irradiation according to Table 3.

TABLE 3

Microwave reaction of eq 3 at 140° C.

eq3

| Time (h) | Solvent | Starting Recovered | Ratio of Substitution: Reduction:Polymer |
|---|---|---|---|
| 1.0 | MeOH | Nothing | small:small:large |
| 0.5 | DME | 70% | 0:0:large |
| 0.5 | DMF | Trace | 17%:0:large |

Some modifications to this method were tried to increase the yield. 5-Iodo-2-aminopyridine was used in the hope that the weaker C—I bond could help to increase the rate of the displacement. The consumption of aromatic iodide was faster (6 h) but unfortunately only polymers formed. Decreasing the reaction temperature did not help (eq 4).

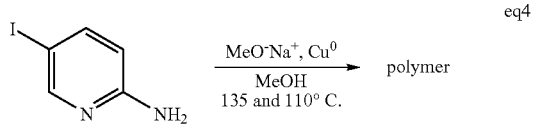

eq4

A different strategy was designed using 5-pyridyl boronate and subsequently oxidized to P5 in the presence of NaOCH$_3$. After a first attempt to prepare the boronate P6 in DMSO[13] with conventional heating failed, the same coupling was tried with microwave heating using DME as the solvent.[14] This procedure gave the desired boronate in 20 min instead of 20 h, but only in 10% yield due to problems found in the work-up (eq 5).

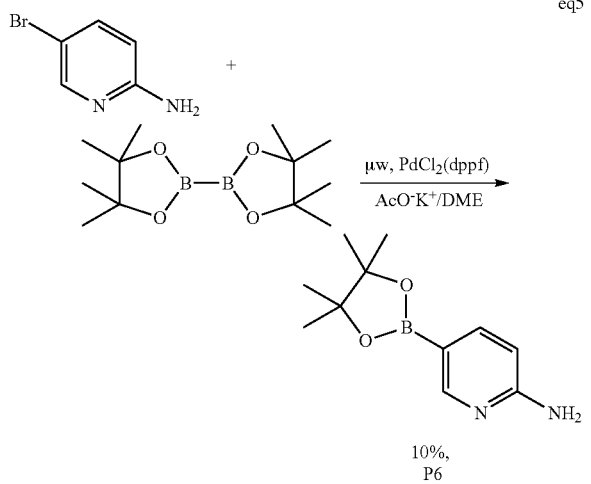

eq5

The free amino group was protected to avoid undesirable coordination of the Pd catalyst and simplify the reaction work-up. In addition, 5-iodo-2-aminopyridine was used to facilitate the Pd insertion in the C-halogen bond. Therefore P1 was protected with trifluoroacetic anhydride to give trifluoroacetamide P7 in 77% yield. This was reacted with pinacolborane in dioxane at 80° C. for 3 h to give the protected pyridyl boronate P8 in 67% yield (eq 6).[15]

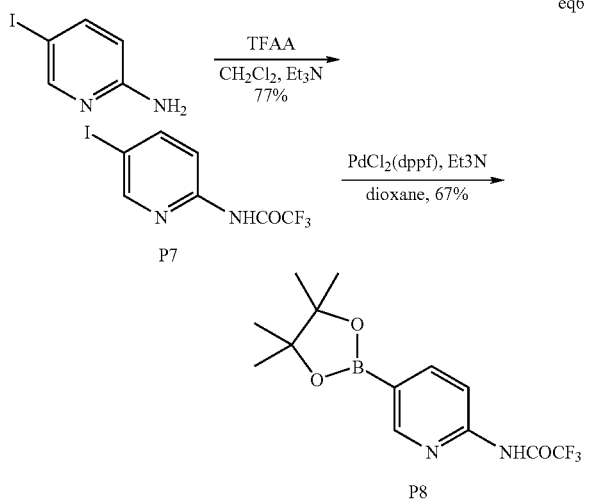

eq6

Oxidation Studies did not generate any desired product. The route was discontinued.

Substitution of halide by SEt group was similar to that of OCH$_3$ group when using copper as catalysts. Although syntheses of P9[16;17] have been reported, the reported methods made use of copper as catalyst and methanol as solvent at 150° C. under pressure.[18] Due to the inconvenience of the procedure, other solvents were evaluated to replace the low boiling point methanol. Ethylene glycol proved to be an excellent choice in this reaction, giving high yield in a short reaction time. The benefits of ethylene glycol as solvent in other copper or copper(I)-catalyzed reaction have been noted.[19] Ethylene glycol was found to be the ligand and solvent when CuI was used as catalyst, to give the aromatic thio-ether, 2-amino-5-ethylthio-pyridine.

The synthesis of 5-chloro-2-aminopyrazine described in the literature is not a very efficient multi-step process.[20] Direct chlorination of the 2-aminopyrazine using N-chlorosuccinimide was used, although the method is known to give overchlorinated by-products. Initial attempt showed that the reaction gave a lot of black polymers after a few min., with the main product being 3,5-dichloro-2-amino pyrazine. Only small amount of 5-chloro-2-aminopyrazine was isolated (eq 7). This reaction could not be scaled up because it was not reproducible. To avoid over chlorination, milder conditions were examined. No reaction was observed at RT, but a complete transformation into the dichloro derivative was observed at 50° C.

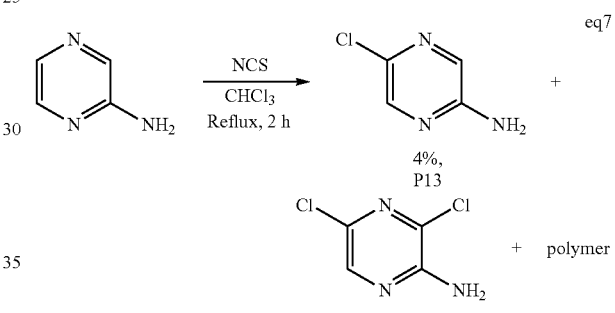

eq7

When the distilled chloroform used for the reaction was pre-treated over basic Al$_2$O$_3$, the black polymers formed in the reaction decreased dramatically. When NCS was added slowly into the refluxing 2-aminopyrazine, the product was isolated at 26%. Moreover, when microwave irradiation was used at 70° C. for 10 min., the yield reached 45% (FIG. 4).

Figure 5:
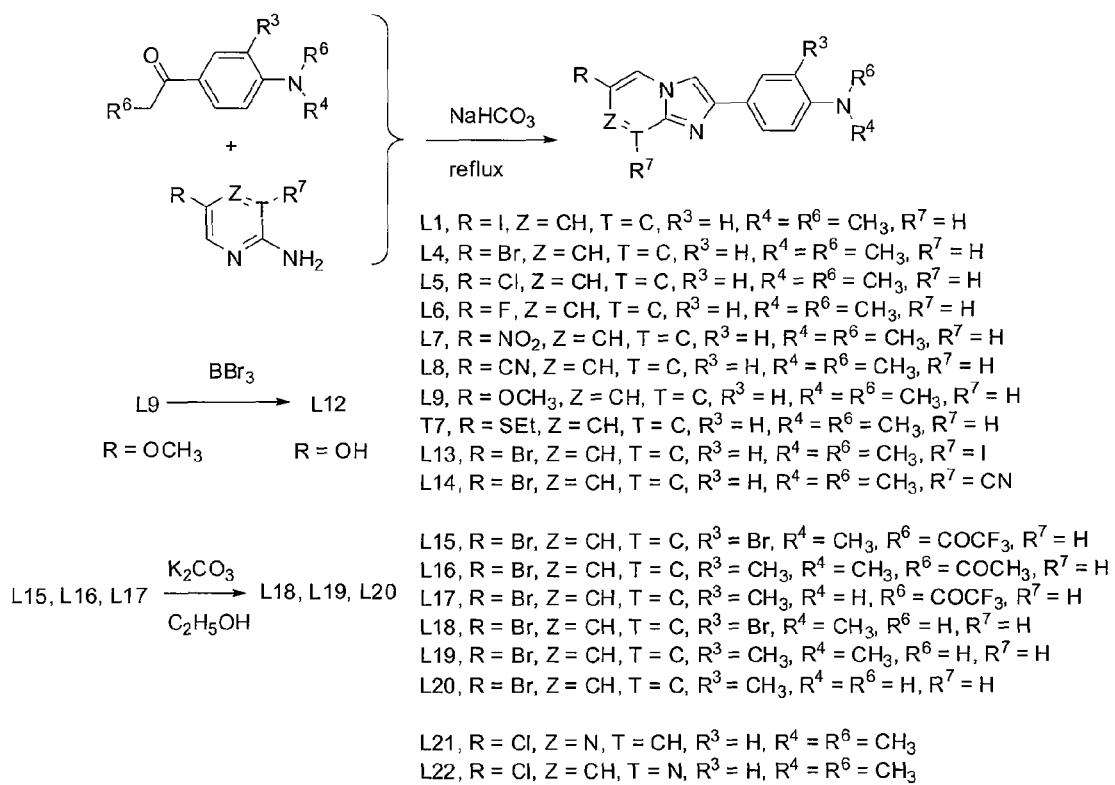

Synthesis of IMPY Derivatives I. Most of the IMPY derivatives were synthesized through the direct condensation of α-bromoketones and 2-amino-pyridines (FIG. 5).[2] In selected examples, when trifluoroacetyl group was used to protect aromatic amino group, no base was needed for the condensation. The difficulty facing the synthesis of L22 came from separation. When excess amine was used, the product could not be separated from the starting amine. When excess α-bromoketone was used, a persistent amount of the starting pyrimidine existed. A small amount of DMF was added in the reaction mixture to dissolve the amine completely, and to induce the precipitation of the product at the same time. By filtering this solution hot, even before reaction complete, we were able to isolate the desired imidazopyrimidine L22 in 23% yields (eq 8).

eq8

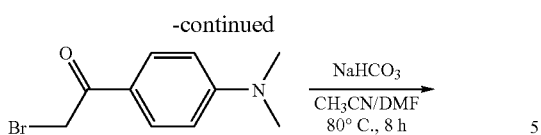
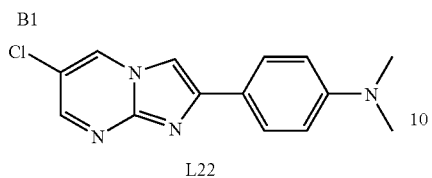

Imidazopyrazine L21 was synthesized from condensation of chloropyrazine P13 and bromoacetophenone B1 (eq 9). The amine 67 was very unreactive though it is very soluble in acetonitrile. Long reaction time and stronger bases such as triethylamine were examined with limited success.

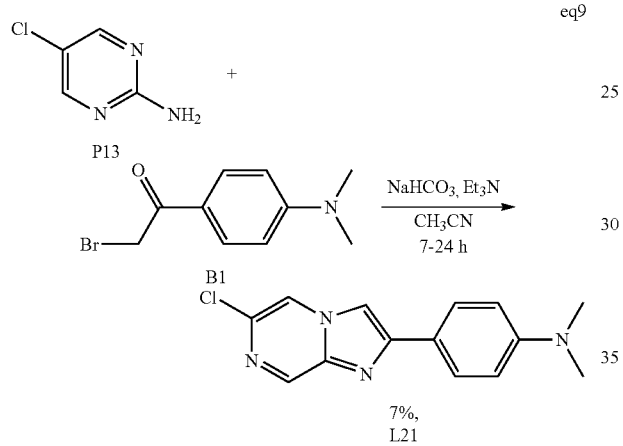

The synthesis of L12 was through demethylation of the methoxy group in L9. The most effective reagent to perform the reaction is BBr$_3$ in DCM (eq 10).[21]

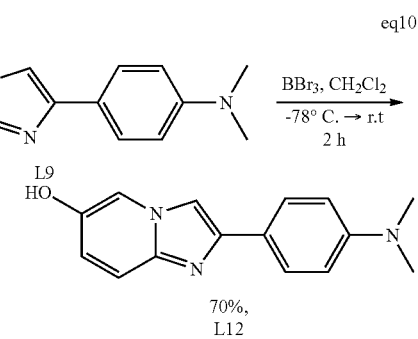

The trifluoroacetyl group on the aromatic amino group in L15, L16, and L17, was easily removed under mild condition of K$_2$CO$_3$ in methanol or ethanol (FIG. 4). This provides an excellent method for the synthesis of IMPY derivatives with amino group(s).

Figure 6:
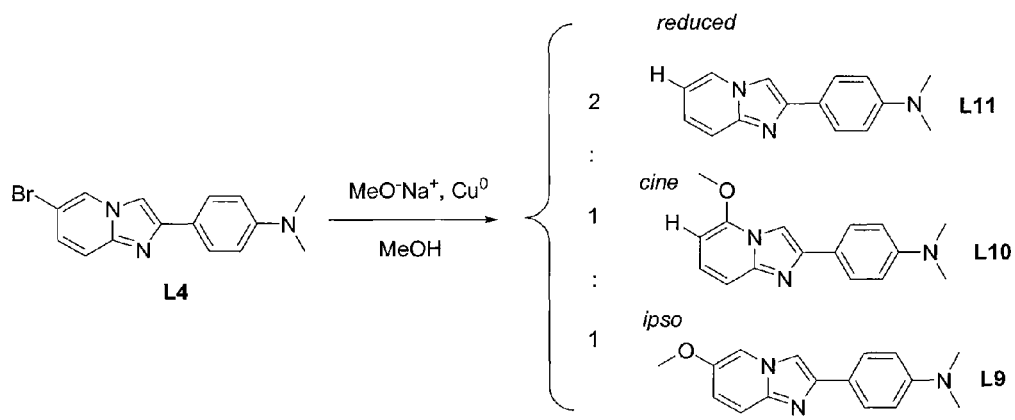
Figure 7:
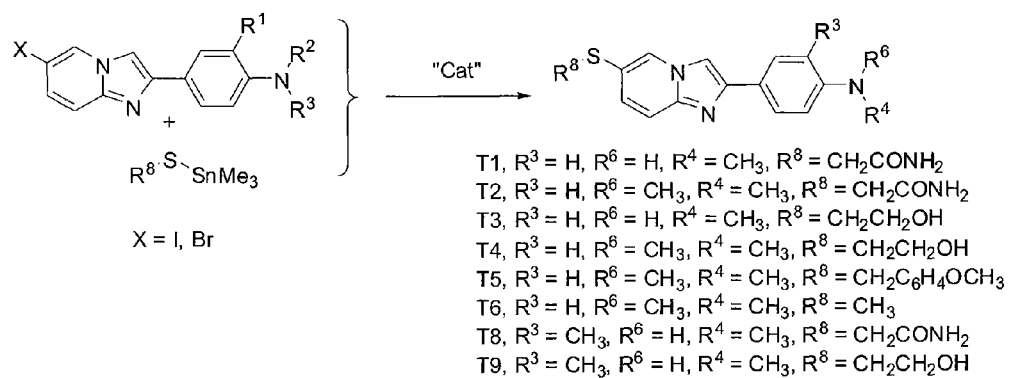

Synthesis of IMPY Derivatives II. For L9, we also attempted direct methoxylation of halide in pre-formed IMPY derivatives. Unfortunately the reaction produced a low yield mixture of reduced (L11), cine (L10) and ipso (L9) substituted analogues which were difficult to separate (FIG. 6). Catalytic substitution of halides by thiolate based on palladium-catalysts was developed to overcome the reduction of the halide (FIG. 7).[22] The new method has been applied to the synthesis of a number of IMPY derivatives with thiolate group.

An advantage of the IMPY derivatives of the present invention relative to the prior art compound [$^{11}$C]PIB (6-OH-BTA-1) is that the derivatives of the present invention can be easily labeled with [$^{18}$F], which has a half-life of about two hours as compared with twenty minutes for [$^{11}$C]. A process for radiolabeling the IMPY derivatives with either label is shown below.

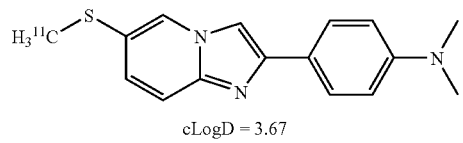

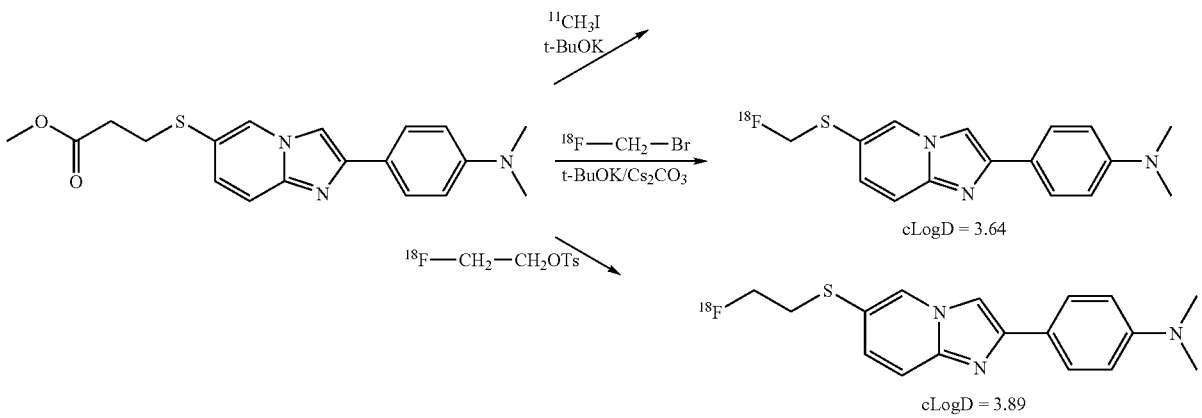

Isolation of Human Amyloid

A method for isolating human β-amyloid plaques from brain tissue[23;24] was modified by incorporating repeated homogenization and centrifugation in 1% SDS buffer and by using DNase and collagenase for digestion. The concentration of β-amyloid plaques was gauged from the concentration of $A\beta_{1-40}$ and $A\beta_{1-42}$ monomers, using ELISA to detect dissolved plaques in formic acid.

In Vitro Assay

Determination of the binding affinities of new ligands for β-amyloid is the first step in selecting candidate radioligands for PET studies in humans. Three types of amyloid plaques have been used to assay ligand binding in vitro, namely synthetic aggregates of $A\beta_{1-40}$, $A\beta_{1-42}$, amyloid plaques from transgenic mice and amyloid plaques from human Alzheimer's disease (AD) brain tissue. Results from the three types and also from different batches of synthetic amyloid plaques vary with respect to binding site concentration.[25] These findings may reflect variations in binding site architecture, though no significant difference in ligand binding affinity has been detected among the three types of amyloid plaques for the binding site typical of 6-OH-BTA-1.[26] Since the ultimate test for a radioligand is successful application in humans, in vitro evaluation using human AD brain tissue is highly appropriate. However, it should be noted that other proteins with similar binding sites might interfere with the binding of the ligand to β-amyloid plaques. This may then be reflected in a lower percentage of displaceable radioactivity in the binding assay.[27] The use of isolated human amyloid plaques may also help to identify other native binding sites.

Isolated plaques were used in developing an in vitro binding assay. Tritiated 6-OH-BTA-1 was selected as the reference radioligand based on its use in human PET imaging and high affinity.[28] Displacement curves were created using non-radioactive 6-OH-BTA-1 and other novel ligands.

The displacement of [$^3$H]6-OH-BTA-1 by non-radioactive 6-OH-BTA-1 or other ligands resulted in classical displacement curves. Some lipophilic ligands required ethanol in the medium to increase their solubility and to effect displacement of reference radioligand. Non-radioactive 6-OH-BTA-1 achieved >95% displacement of reference radioligand, indicating that the presence of competing binding sites for the isolated amyloid plaques was negligible. This assay could therefore be used to screen compounds for amyloid binding without interference from other proteins, such as tau-tangles. This displacement curve was also analyzed using a homologous displacement mathematical model to extract the $B_{max}$ of the amyloid plaques. The measured $B_{max}$ is linear with the amount of amyloid used in the experiment. The ratio between $B_{max}$ and the amount of $A\beta_{1-42}$ monomer measured by ELISA is about 1:2, somewhat less than that reported previously.[25] The denaturing agents used to aid dissolution of the amyloid plaques may account for the observed difference.

The binding affinities for a variety of IMPY derivatives are listed in Table 3. In this table, Ki is a measure (in nM units) of the binding affinity of the compound toward beta-amyloid plaques in AD brain tissue, measured through a competitive radioligand displacement in vitro assay using [$^3$H]6-OH-BTA-1 as the reference radioligand. The lipophilicity of the compound is represented by $cLogD_{7.4}$ which is calculated through a software package (ACD/LogD version 8.0) at pH=7.4, a close mimic of physiological conditions.

TABLE 4

IMPY derivatives.

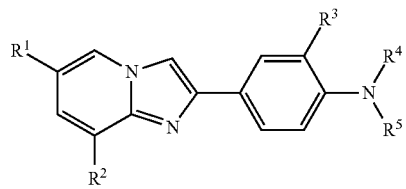

IMPY Derivatives, 1

$R^1$ = F, Cl, Br, I, SEt, SMe, $SCH_2CH_2OH$, $SCH_2CONH_2$, OH, OMe
$R^2$ = H, CN, I
$R^3$ = H, Me, Br
$R^4$ = H, Me
$R^5$ = Me, $CH_2CH_2F$, $CH_2CH_2CH_2F$

| Ligand | $R^1$ | $R^2$ | $R^3$ | $R^4$ | $R^5$ | $cLogD_{7.4}$ | Ki (nM) |
|---|---|---|---|---|---|---|---|
| L1 (IMPY) | I | H | H | Me | Me | 4.37 ± 0.88 | 8.9 ± 0.7 |
| L4 | Br | H | H | Me | Me | 4.11 ± 0.88 | 5.9 ± 0.4 |
| L5 | Cl | H | H | Me | Me | 3.93 ± 0.84 | 24.2 ± 5.6 |
| L6 | F | H | H | Me | Me | 3.38 ± 0.88 | 13.0 ± 1.6 |
| L7 | $NO_2$ | H | H | Me | Me | 3.09 ± 1.30 | 7.6 ± 0.7 |
| L8 | CN | H | H | Me | Me | 2.80 ± 1.31 | 8.2 ± 1.0 |
| L9 | OMe | H | H | Me | Me | 3.05 ± 1.30 | 38.5 ± 5.0 |
| L12 | OH | H | H | Me | Me | 1.26 ± 1.29 | 177 ± 31 |
| T7 | SEt | H | H | Me | Me | 4.24 ± 1.31 | 8.3 ± 0.5 |
| L13 | Br | I | H | Me | Me | 5.17 ± 0.93 | 183 ± 61 |
| L14 | Br | CN | H | Me | Me | 3.28 ± 1.35 | >180 |
| L18 | Br | H | Br | H | Me | 4.30 ± 0.94 | 7.4 ± 0.6 |
| L19 | Br | H | Me | H | Me | 4.16 ± 0.88 | >1000 |
| L20 | Br | H | Me | H | H | 3.28 ± 0.87 | 658 ± 47 |
| T1 | $SCH_2CONH_2$ | H | H | H | Me | 1.59 ± 1.33 | 1840 ± 497 |
| T2 | $SCH_2CONH_2$ | H | H | Me | Me | 2.02 ± 1.33 | 391 ± 76 |
| T3 | $SCH_2CH_2OH$ | H | H | H | Me | 2.54 ± 1.35 | 645 ± 75 |

TABLE 4-continued

IMPY derivatives.

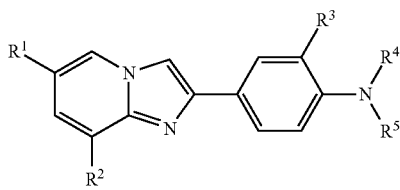

IMPY Derivatives, 1

$R^1$ = F, Cl, Br, I, SEt, SMe, $SCH_2CH_2OH$, $SCH_2CONH_2$, OH, OMe
$R^2$ = H, CN, I
$R^3$ = H, Me, Br
$R^4$ = H, Me
$R^5$ = Me, $CH_2CH_2F$, $CH_2CH_2CH_2F$

| Ligand | $R^1$ | $R^2$ | $R^3$ | $R^4$ | $R^5$ | $cLogD_{7.4}$ | Ki (nM) |
|---|---|---|---|---|---|---|---|
| T4 | $SCH_2CH_2OH$ | H | H | Me | Me | 2.96 ± 1.35 | 88 ± 6 |
| T5 | $SCH_2C_6H_4OCH_3$ | H | H | Me | Me | 4.76 ± 1.35 | 8.3 ± 1.8 |
| T6 | SMe | H | H | Me | Me | 3.67 ± 1.31 | 7.9 ± 0.6 |
| T8 | $SCH_2CONH_2$ | H | Me | H | Me | 2.12 ± 1.33 | >1000 |
| T9 | $SCH_2CH_2OH$ | H | Me | H | Me | 3.07 ± 1.35 | >1000 |
| L2 | I | H | H | Me | $CH_2CH_2F$ | 4.52 ± 0.92 | 31 ± 5 |
| L3 | I | H | H | Me | $CH_2CH_2CH_2F$ | 4.90 ± 0.92 | 41 ± 5 |

The BTA derivatives were synthesized through the condensation of 2-amino-aryl-thiols and aryl carboxylic acid under acidic conditions.

TABLE 5

| Compound | $cLogD_{7.4}$ | Ki (nM) |
|---|---|---|
| L21 | 2.54 ± 1.30 | 88 ± 22 |
| L22 | 3.14 ± 1.43 | 147 ± 20 |
| P1 | 4.36 | 5.7 ± 0.7 |
| PIB | 3.31 | 7.23 ± 1.0 |

Comparison of the Ki values of L1, L18 and L19 in Table 4 shows that the "isosteric effect" works partially. Since Br and Me are similar in size, the data show that a polar group increases binding. Similar analysis of the binding affinities of L1, L5, L6, and T7 shows that the thiol ether group provides optimal electronic and steric effects for binding, but the effect disappears as soon as a hydrophilic group is attached (cf results for T4 and T8). Increasing the size of substituents on the aromatic amino group decreases binding affinity, as reflected in L1, L2 and L3. However, there is substantial requirement for size in the 6-position (c.f. L6, L12 and L9). For L12, the combination of small and polar properties for the 6-substituent abolishes all binding affinity. Interestingly, introduction of a CN group into 8-position also completely removes the binding affinity (as in L14), reflecting minimal tolerance for any substituents at the periphery of the IMPY skeleton.

The reference citations above are identified below under Reference List No. 1.

Reference List No. 1

1. Selkoe, D. J. Alzheimer's disease: genes, proteins, and therapy. Physiol Rev. 2001, 81, 741-766.
2. Cai, L.; Chin, F. T.; Pike, V. W.; Toyama, H.; Liow, J. S.; Zoghbi, S. S.; Modell, K.; Briard, E.; Shetty, H. U.; Sinclair, K.; Donohue, S.; Tipre, D.; Kung, M. P.; Dagostin, C.; Widdowson, D. A.; Green, M.; Gao, W.; Herman, M. M.; Ichise, M.; and Innis, R. B. Synthesis and evaluation of two $^{18}$F-labeled 6-iodo-2-(4'-N,N-dimethylamino)phenylimidazo[1,2-a]pyridine derivatives as prospective radioligands for beta-amyloid in Alzheimer's disease. J. Med. Chem. 2004, 47, 2208-2218.
3. Hu, Jianguo, Li, Zuoy, Li, Yulin, Tang, Luoxiang, and Wu, Meijuan. Method of synthesizing 5-[1-hydroxy-2-(isopropylamino)ethyl]aminobenzonitrile. Faming Zhuanli Shenqing Gongkai Shuomingshu CN95-103024-19950403 [CN1120535A19960417]. 1996. CAN130:139172.
4. Cai, L.; Brouwer, C.; Sinclair, K.; Cuevas, J.; and Pike, V. W. Titanium(IV) chloride-promoted synthesis of new imidazo[1,2a]pyridine derivatives under microwave conditions. *Synthesis* 2005, 61, 0000.
5. Hu, Z. Process for synthesizing ketoprofen. Faming Zhuanli Shenqing Gongkai Shuomingshu CN-95-109877-19950824[CN1143624A19970226]. 1997. CAN128: 153928.
6. Kuhla, D. E., Campbell, H. F., Studt, W. L., and Molino, B. F., Bicyclic heteroaryl thiazole compounds and their cardiotonic uses. PCT Int. Appl. WO 85-US2522-19851218 [WO8603749A1-19860703]. 1986. CAN105:226538.
7. Otsuka-Pharmaceutical-Co, Ltd. Carbostyril derivatives and a cardiotonic composition containing them. Belg. BE82-207321-19820215[BE892148A1-19820816]. 1982. CAN98:34510.
8. Ellis, G. P. and Romneyalexander, T. M. Cyanation of aromatic halides. *Chem. Rev.* 1987, 87, 779-794.
9. Liang, C.-H., Duffield, J., Romero, A., Chiu, Y.-H., Rabuka, D., Yao, S., Sucheck, S., Marby, K, Shue, Y.-K., Ichikawa, Y., and Hwang, C.-K. Preparation of macrolide erythronolide carbamates as antitumor and antibacterial agents. (Optimer Pharmaceuticals, Inc. USA. 2004-US6645[2004080391], 108. 2004. WO, CAN141:296244. Mar. 5, 2004.
10. Ueno, T., Kimura, Y., and Kasuga, Y. Process for the preparation of aminocyanopyridines. (Nippon Fine Chemical Co., Ltd. Japan and Mitsubishi Chemical Corp.). 2000-128683[2001302639], 4. 2001. JP, CAN135: 331348. Apr. 28, 2000.
11. Van de Poel, H.; Guillaumet, G.; and Viaud-Massuard, M. C. Synthesis of melatonin analogues derived from furo[2, 3-b]- and [2,3-c]pyridines by use of a palladium-copper catalyst system. *Heterocycles* 2002, 57, 55-71.
12. Capdevielle, P. and Maumy, M. Esters are effective cocatalysts in copper-catalyzed methanolysis of aryl bromides. *Tetrahedron Letters* 1993, 34, 1007-1010.
13. Ishiyama, T.; Murata, M.; and Miyaura, N. Palladium(O)-catalyzed cross-coupling reaction of alkoxydiboron with haloarenes—A direct procedure for arylboronic esters. *J. Org. Chem.* 1995, 60, 7508-7510.
14. Appukkuttan, P.; Van der Eycken, E.; and Dehaen, W. Microwave enhanced formation of electron rich arylboronates. *Synlett* 2003, 1204-1206.
15. Baudoin, O.; Guenard, D.; and Gueritte, F. Palladium-catalyzed borylation of ortho-substituted phenyl halides and application to the one-pot synthesis of 2,2'-disubstituted biphenyls. *J. Org. Chem.* 2000, 65, 9268-9271.
16. Sundberg, R. J.; Dahlhausen, D. J.; Manikumar, G.; Mavunkel, B.; Biswas, A.; Srinivasan, V.; King, F., Jr.; and Waid, P. Preparation of 2-aryl- and 2-(aryloxymethyl)imidazo[1,2-a]pyridines and related compounds. *J. Heterocycl. Chem.* 1988, 25, 129-137.
17. Gol'dfarb, Y.; Stoyanovich, F. M.; Marakatkina, M. A.; and Gorushkina, G. I. Synthesis of 6-(alkylthio)imidazo[1, 2-a]pyridines. *Khimiya Geterotsiklicheskikh Soedinenii* 1979, 634-638.
18. Bochis, R. J.; Olen, L. E.; Waksmunski, F. S.; Mrozik, H.; Eskola, P.; Kulsa, P.; Wilks, G.; Taylor, J. E.; Egerton, J. R.; Ostlind, D. A.; and Olson, G. Substituted Imidazo[1,2-a]pyridine-2-carbamate anthelmintics. *J. Med. Chem.* 1981, 24, 1518-1521.
19. Enguehard, C.; Allouchi, H.; Gueiffier, A.; and Buchwald, S. L. Easy access to novel substituted 6-aminoimidazo[1, 2-a]pyridines using palladium- and copper-catalyzed aminations. *J. Org. Chem.* 2003, 68, 4367-4370.
20. Barlin, G. B.; Davies, L. P.; Ireland, S. J.; Ngu, M. M. L.; and Zhang, J. K. Imidazo[1,2-b]pyridazines. 12. Syntheses and central-nervous-system activities of some substituted imidazo[1,2-b]pyridazines and related imidazo[1,2-a]pyridines, imidazo[1,2-a]pyrimidines and imidazo[1,2-a]pyrazines. *Austr. J. Chem.* 1992, 45, 877-888.
21. Vickery, E. H.; Pahler, L. F.; and Eisenbraun, E. J. Selective O-demethylation of catechol ethers—comparison of boron tribromide and iodotrimethylsilane. *J. Org. Chem.* 1979, 44, 4444-4446.
22. Cai, L.; Cuevas, J.; Peng, Y.; and Pike, V. W. Rapid palladium-catalyzed cross-coupling in the synthesis of aryl thioethers under microwave conditions. *Org. Letters* 2005.
23. Soderberg, L.; Zhukareva, V.; Bogdanovic, N.; Hashimoto, T.; Winblad, B.; Iwatsubo, T.; Lee, V. M.; Trojanowski, J. Q.; and Naslund, J. Molecular identification of AMY, an Alzheimer disease amyloid-associated protein. *J. Neuropathol. Exp. Neurol.* 2003, 62, 1108-1117.
24. Roher, A. E. Structural alterations in the peptide backbone of beta-amyloid core protein may account for its deposition and stability in Alzheimer's disease. *J. Biol. Chem.* 1993, 268, 3072-3083.
25. Mathis, C. A.; Wang, Y.; Holt, D. P.; Huang, G. F.; Debnath, M. L.; and Klunk, W. E. Synthesis and evaluation of $^{11}$C-labeled 6-substituted 2-arylbenzothiazoles as amyloid imaging agents. *J. Med. Chem.* 2003, 46, 2740-2754.
26. Klunk, W. E.; Wang, Y.; Huang, G. F.; Debnath, M. L.; Holt, D. P.; Shao, L.; Hamilton, R. coupling L.; Ikonomovic, M. D.; DeKosky, S. T.; and Mathis, C. A. The binding of 2-(4'-methylaminophenyl)benzothiazole to postmortem brain homogenates is dominated by the amyloid component. *J. Neurosci.* 2003, 23, 2086-2092.
27. Klunk, W. E.; Wang, Y.; Huang, G. F.; Debnath, M. L.; Holt, D. P.; and Mathis, C. A. Uncharged thioflavin-T derivatives bind to amyloid-beta protein with high affinity and readily enter the brain. *Life Sci.* 2001, 69, 1471-1484.
28. Munk, W. E.; Engler, H.; Nordberg, A.; Wang, Y.; Blomqvist, G.; Holt, D. P.; Bergstrom, M.; Savitcheva, I.; Huang, G. F.; Estrada, S.; Ausen, B.; Debnath, M. L.; Barletta, J.; Price, J. C.; Sandell, J.; Lopresti, B. J.; Wall, A.; Koivisto, P.; Antoni, G.; Mathis, C. A.; and Langstrom, B. Imaging brain amyloid in Alzheimer's disease with Pittsburgh Compound-B. *Ann. Neurol.* 2004, 55, 306-319.

A further aspect of this invention is the novel synthesis of aryl thioether derivatives of IMPY compounds by a rapid palladium-catalyzed cross-coupling under microwave conditions. In the following description, the cited references are identified under Reference List No. 2.

Aromatic thioethers of IMPY compounds are valuable as synthetic intermediates and as therapeutic drugs.[1,2] Homogeneous catalysts based on either copper(I) or palladium have been developed for their syntheses.[2,3] Mechanistic studies of palladium-catalyzed aromatic substitution of halo or triflate groups by thiolate show that both three and four coordinate intermediates might be involved.[4-6] Indeed, both mono and bidentate phosphine ligands have been developed for this type of reaction.[7-12] Copper(I)-based catalysts for similar syntheses are mechanistically much less clear.[13-17]

In the synthesis of these compounds, introducing the thioether group in the last step avoids manipulation and protection of this sensitive group in the synthesis of the IMPY skeleton. The aromatic halide substrates to be substituted are generally accessible in multiple step syntheses.[18] Successful substitution of aryl halides with thiolates requires the avoidance of a competing reductive removal of the halogen substituent. The objects of this aspect of the invention are to achieve (a) an one-step introduction of a thioether group into a halogen position in an aryl ring; (b) selective introduction of a thioether group at an iodo position in the presence of other halogen substituents, such as bromo; (c) tolerance of functional groups, especially amino groups; and (d) fast microwave-assisted reaction conditions. Disclosed herein is a general, efficient, and operationally simple palladium-catalyzed aryl thioether synthesis that achieves these objects.

Two reaction schemes are described below. The first is a copper(I)-mediated coupling of aryl iodides with thiols (Scheme B1), while the second is a palladium-catalyzed coupling of aryl iodides with tin thiolates (Scheme B2).

Scheme B1:

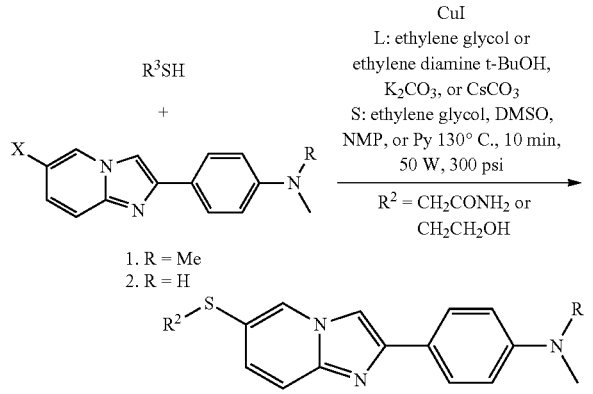

1. R = Me
2. R = H

Scheme B2:

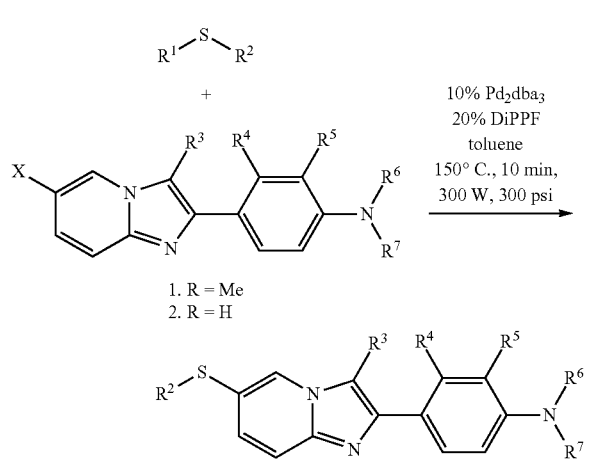

1. R = Me
2. R = H

X = I, Br
$R^1$ = H or SnMe$_3$
$R^2$ = CH$_2$CH$_2$OH, CH$_2$CONH$_2$, CH$_2$C$_6$H$_4$OCH$_3$
$R^3$ = $R^4$ = H or $R^3R^4$ = CH$_2$CH$_2$
$R^5$ = H, Me, Br
$R^6$ = H, Me
$R^7$ = H, Me, Ac

The aryl halide 4-(6-iodoindolizin-2-yl)-N-methylbenzenamine was used as the substrate, with either 2-mercaptoacetamide or 2-mercaptoethanol as the thiolating agent. In the copper-catalyzed reaction (Scheme B1), the catalyst used was CuI. Two ligands, ethylene glycol and ethylene diamine, were evaluated along with a variety of bases and solvents (Table B1). Low conversion of the iodo compound was observed with a catalytic amount of CuI. The reaction went to completion only when a greater than stoichiometric amount of CuI was used. For 2-mercaptoacetamide, the majority of the reaction product arose from reductive removal of the iodo group. For 2-mercaptoethanol, substitution of the iodo group was nearly quantitative for one substrate when 5 equivalents of CuI were used. However, no catalytic or general reaction was observed and so no further effort was expended on this approach for other substrates.

TABLE B1

The copper (I)-mediated coupling of aryl iodides (1 or 2) with thiols: Percent yield of conversion followed by ratio of substitution to reduction in parentheses.

| | Method: | | |
|---|---|---|---|
| Substituents: | (1) | (2) | (3) |
| $R^2$ = —CH$_2$CONH$_2$<br>R = Me | 100<br>(1:4.0) | 81<br>(0:1) | |
| $R^2$ = —CH$_2$CONH$_2$<br>R = H | 81<br>(1:8.3) | 100<br>(1:4.1)[a,b] | 100<br>(0:1) |
| $R^2$ = —CH$_2$CH$_2$OH<br>R = Me | 60<br>(messy) | | |
| $R^2$ = —CH$_2$CH$_2$OH<br>R = H | 96<br>(1:0.038) | | |

The general conditions were 130° C., 10 min, 50 W, 300 p.s.i., substrate: thiol=1: 1.2-5. In Method (1), 1-5 equiv CuI, 2 equiv ethylene diamine, 2 equiv t-BuOK or K$_2$CO$_3$ in DMSO, and N-methylpyrrolidin-2-one (NMP) or dioxane were used. In Method (2), 1-5 equiv CuI, 2 equiv ethylene glycol, and 2 equiv t-BuOK in Py were used. In Method (3), 0.05 equiv CuI, and 2 equiv Cs$_2$CO$_3$ in NMP were used. [a]Without the thiol, the reaction generated reduced and HOCH$_2$CH$_2$O-substituted products. [b]No reaction was observed when 1,2-dimethoxyethane was used instead of ethylene glycol.

The palladium-catalyzed coupling of aryl iodides with thiols (Scheme B2) was evaluated using the protocol originally established by Buchwald et al,[7] who used aryl bromides as substrates. Variations here included the use of i) catalysts, such as (DPPF)PdCl$_2$; ii) catalyst precursors, such as Pd$_2$dba$_3$ and Pd(OAc)$_2$; iii) ligands (L) as shown in Scheme B2; iv) bases, such as NEt$_3$, t-BuOK; and v) solvents, such as NMP, dioxane, or toluene. Multiple products in similar amounts were generated, including the desired substitution products. Given the success of a number of bulky monophosphines in the catalysis of aryl C—N and C—O formation,[6;19] a number of bulky monophosphines were evaluated, as shown below:

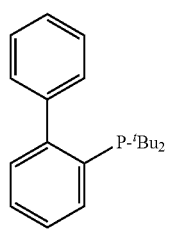
L1

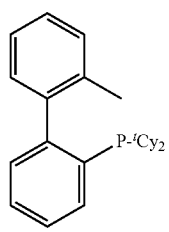
L2

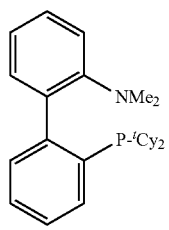

L3

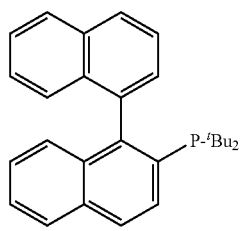

L4

Under the general conditions used (150° C., 10 min, 300 W, 300 p.s.i. with 0.05 equiv $Pd_2dba_3$, 0.1 equiv L, 2-4 equiv of $NEt_3$ or t-BuOK, and ethanol or toluene as solvent), the new ligands behave similarly to $PPh_3$, giving less than 10% total conversion of aryl iodide and ratios of substitution and reduction ranging from 0.4 to 15. No further reaction progress was observed on extended reaction time.

A number of thiolates have been used for the aromatic substitution reaction.[1;20] When the tin thiolates were used in Scheme B2, mainly substitution products accompanied by minor reduction products were observed. Different kinds of bis-phosphine ligands were evaluated, as shown below:

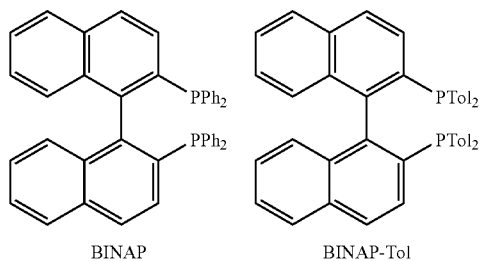

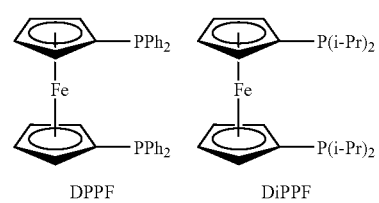

The results are shown in Table B2.

TABLE B2

Scheme B2 with $R^1$ = SnMe, $R^3$ = $R^4$ = $R^5$ = $R^6$ = H, $R^7$ = Me, X = I: The palladium-catalyzed coupling of aryl iodides (1 or 2) with tin thiolates. General conditions: 150° C., 10 min, 300 W, 300 psi, substrate:thiolate = 1:1, in toluene. Results shown are percent yield of conversion followed by ratio of substitution to reduction in parentheses.

| | $R^2$; $R^6$: | | | |
|---|---|---|---|---|
| Ligand: | $CH_2CONH_2$; H | $CH_2CONH_2$; Me | $CH_2CONH_2$; H | $CH_2CONH_2$; Me |
| BINAP | | | | 17 (1:0.13)[a] |
| BINAP-Tol | | | | 81 (1:0.12)[b] |
| DPPF | | | 100 (1:0)[c] | 56 (1:0.15)[d] |
| DiPPF | 51 (1:0.019)[e] | 76 (1:0.14)[f] | 6 (1:0.083)[g] | |

[a]0.1 equiv $Pd_2(dba)_3$, 0.1 equiv L.
[b]0.2 equiv $Pd_2(dba)_3$, 0.4 equiv L.
[c]0.11 equiv $Pd_2(dba)_3$, 0.14 equiv L.
[d]0.1 equiv $Pd_2(dba)_3$, 0.1 equiv L.
[e]0.1 equiv $Pd_2(dba)_3$, 0.2 equiv L.
[f]0.2 equiv $Pd_2(dba)_3$, 0.4 equiv L.
[g]0.2 equiv $Pd_2(dba)_3$, 0.4 equiv L.

BINAP-Tol, DPPF, and DiPPF are efficient ligands for the reaction. Since a number of chelating phosphines have been used in enantioselective hydrogenation,[21] they provide further excellent candidates for evaluation in this reaction. The yields and relative degrees of substitution and reduction for various phosphines when used in Scheme B2 are shown below in Table B3. Once again, ferrocene-based bis-phosphine, f-binaphane, provided the best combination of reactivity and selectivity.

TABLE B3

Scheme B2 with $R^1$ = SnMe, $R^2$ = $CH_2CONH_2$, $R^3$ = $R^4$ = $R^5$ = $R^6$ = H, $R^7$ = Me, X = I:
The palladium-catalyzed coupling of aryl iodide with tin thiolates.

| Ligands | Products |
|---|---|
| T-Phos | 22 (1:0.91) |
| TangPhos | 7 (1:0.71) |
| Binapine | 1 (1:0.63) |
| f-Binaphane | 11 (1:0.077) |
| C4TunePhos | 8 (1:0.77) |
| DuanPhos | 0 |
| Binaphane | 0 |

General conditions: 150° C., 10 min, 300 W, 300 psi, substrate:thiolate=1:1, 0.1 equiv $Pd_2(dba)_3$ and 0.1 equiv. ligand in toluene. Results shown are percent yield of conversion followed by ratio of substitution to reduction in parentheses. The structures of the ligand are shown in Ref. 21.

Palladium catalysts based on phosphine oxide ligands are a new type of efficient, versatile, air-stable and preformed homogeneous catalysts for the C—S bond formation.[8-10] Ten of the most common catalysts were evaluated in Scheme B2. The results are shown in Table B4 which indicates that low reactivities and selectivities were generally observed.

TABLE B4

The palladium-catalyzed coupling of aryl iodide (2) with tin thiolates, using Scheme B2 with $R^1$ = SnMe, $R^2$ = $CH_2CONH_2$, $R^3$ = $R^4$ = $R^5$ = $R^6$ = H, $R^7$ = Me, X = I.
General conditions: 150° C., 10 min, 300 W, 300 psi, substrate:thiolate = 1:1.5, in toluene. In Method (i), 2.5 equiv $K_2CO_3$ was used; in Method (ii), 2.5 equiv $K_2CO_3$ and 2.5 equiv TEA were used, and in Method (iii), 2 equiv t-BuOK were used.
The catalyst structures are shown in Refs. 8-10.
The results shown are percent yield of conversion followed by ratio of substitution to reduction in parentheses.

|  | Method: | | |
|---|---|---|---|
| Catalyst: | (i) | (ii) | (iii) |
| POPd | 0 |  | 0 |
| PXPd | 2 (1:0.63) |  |  |
| PXPd7 | 7 (1:0.77) | 1 (1:0.83) | 3 (1:0.50) |
| POPd2 | 0[a,b] | 0 | 1 (1:0) |
| PXPd2 | 2 (1:1.7) |  |  |
| POPd6 | 0 |  |  |
| PXPd6 | 2 (1:2.5) |  |  |
| POPd1 | 0 | 0 | 0 |
| POPd7 | 0 | 0 |  |
| Ph1-Phoxide | 3 (1:0.59) |  |  |

[a]When the thiol was used, no reaction was observed.
[b]Other thiols, such as $HSCH_2CH_2OH$, also did not react.

When aryl bromides were used to compare the reactivity of thiols vs. tin-thiolates, the thiols showed better reactivity but less selectivity, as in reactions with the iodides. The results are shown in Table B5.

TABLE B5

The palladium-catalyzed coupling of aryl bromides with thiols or tin thiolates, using Scheme B2 with $R^3$ = $R^4$ = H, $R^5$ = Me, $R^6$ = H, $R^7$ = Me, X = Br.
General conditions: 150° C., 10 min, 300 W, 300 psi, substrate:thiolate = 1:1.5, in toluene.
The results shown are percent yield of conversion, followed by ratio of substitution to reduction in parentheses.

|  | Ligand: | | | |
|---|---|---|---|---|
| $R^1$; $R^2$: | BINAP | BINAP Tol | DPPF | DiPPF |
| $R^1$ = SnMe$_3$ $R^2$ = $CH_2CH_2OH$ | 6 (1:0)[a] | 16 (1:0)[b] | 0.4 | 14 (1:0)[d] |
| $R^1$ = SnMe$_3$ $R^2$ = $CH_2CONH_2$ |  |  |  | 26 (1:0)[e] |
| $R^1$ = H $R^2$ = $CH_2CH_2OH$ |  |  |  | 100 (1:0.06)[f] |
| $R^1$ = H $R^2$ = $CH_2CONH_2$ |  |  |  | 26 (1:0.67)[h] |

[a]0.1 equiv Pd$_2$(dba)$_3$ and 0.1 equiv L.
[b]0.2 equiv Pd$_2$(dba)$_3$ and 0.2 equiv L.
[c]0.1 equiv Pd$_2$(dba)$_3$ and 0.1 equiv L.
[d]0.2 equiv Pd$_2$(dba)$_3$ and 0.4 equiv L.
[e]0.2 equiv Pd$_2$(dba)$_3$ and 0.4 equiv L.
General conditions for thiol reaction: 150° C., 10 min, 300 W, 300 p.s.i., 11.2 equiv t-BuOK;
[f]0.2 equiv Pd (OAc)$_2$ and 0.23 equiv L in dioxane.
[g]0.2 equiv Pd$_2$(dba)$_3$ and 0.23 equiv L in toluene.
[h]0.2 equiv Pd$_2$(dba)$_3$ and 0.23 equiv L in dioxane.

The combination of Pd$_2$dba$_3$ (dipalladium dibenzylideneacetone) as catalyst, DiPPF as ligand and tin thiolate as reagent was used to synthesize several aryl thiolates in moderate to high yield. The results are shown in Table B6.

TABLE B6

The palladium-catalyzed synthesis of thioethers with Pd$_2$dba$_3$ as catalyst, DiPPF as ligand, and tin thiolate, using Scheme B2 with $R^1$ = SnMe$_3$, $R^3$ = $R^4$ = H, $R^7$ = Me. X, $R^2$, $R^5$, and $R^6$ are as shown in the table.
General conditions: 150° C., 10 min, 300 W, 300 psi, substrate:thiolate = 1:1-1.5, in toluene. In Method C1, 0.1 equiv Pd$_2$(dba)$_3$ and 0.1 equiv DiPPF were used; in Method C2, 0.2 equiv Pd$_2$(dba)$_3$ and 0.4 equiv DiPPF were used; in Method C3, 0.2 equiv Pd$_2$(dba)$_3$ and 0.2 equiv DiPPF were used; in Method C4, 0.2 equiv Pd$_2$(dba)$_3$ and 0.8 equiv DiPPF were used. The results shown are the isolated yield of the substitution product from reverse phase HPLC.

| X | $R^5$ | $R^6$ | $R^2$ | Method | Yield (%) |
|---|---|---|---|---|---|
| I | H | H | $CH_2CONH_2$ | C1 | 78 |
| I | H | Me | $CH_2CONH_2$ | C2 | 85 |
| I | H | H | $CH_2CH_2OH$ | C1 | 91 |
| I | H | Me | $CH_2CH_2OH$ | C2 | 89 |
| I | H | Me | $CH_2C_6H_4OCH_3$ | C3 | 85[a] |
| Br | Me | H | $CH_2CONH_2$ | C4 | 69 |
| Br | Me | H | $CH_2CH_2OH$ | C4 | 69 |

[a]When $B_2O_3$ was used with the thiol instead of tin thiolate, no reaction was observed.

When bromo and iodo groups were both present in the same compound, selective substitution of the iodo group was realized using the same reaction conditions developed above, using stoichiometric quantities of tin-thiolates. The results are shown in Table B7.

TABLE B7

The palladium-catalyzed synthesis of thioethers with Pd$_2$(dba)$_3$ as catalyst, DiPPF as ligand, and tin thiolate, using Scheme B2 with $R^1$ = SnMe$_3$, $R^3R^4$ = $CH_2CH_2$, $R^5$ = Br, $R^6$ = Me, and $R^7$ = Ac. $R^2$ is as shown in the table. General conditions: 150° C., 10 min, 300 W, 300 psi, substrate:thiolate = 1:1, 0.1 equiv Pd$_2$(dba)$_3$, 0.1 equiv DiPPF, in toluene. The results shown are the isolated yield of the substitution product from reverse phase HPLC.

| X | $R^2$ | Yield (%) |
|---|---|---|
| I | $CH_2CONH_2$ | 60 |
| I | $CH_2CH_2OH$ | 94 |

The process method for the rapid, selective and efficient substitution of bromo or iodo groups in aryl halides by tin-thiolates with microwave heating, as disclosed herein, is applicable to substrates with an easily reducible iodo group, in either the presence or absence of a bromo group. Lower reactivity and higher selectivity were observed as compared with those using thiols as reagents. The corresponding reactions under conventional heating did not generate any appreciable amount of products except for those without any heteroatoms in the substrates (no data shown).

Reference List No. 2

1. Dickens, M. J.; Gilday, J. P.; Mowlem, T. J.; Widdowson, D. A. *Tetrahedron* 1991, 47, 8621-8634.
2. Kondo, T.; Mitsudo, T. *Chem. Rev.* 2000, 100, 3205-3220.
3. Baranano, D.; Mann, G.; Hartwig, J. F. *Curr. Org. Chem.* 1997, 1, 187-305.
4. Baranano, D.; Hartwig, J. F. *J. Am. Chem. Soc.* 1995, 117, 2937-2938.
5. Louie, J.; Hartwig, J. F. *J. Am. Chem. Soc.* 1995, 117, 11598-11599.
6. Hartwig, J. F. *Acc. Chem. Res.* 1998, 31, 852-860.
7. Murata, M.; Buchwald, S. L. *Tetrahedron* 2004, 60, 7397-7403.
8. Li, G. Y. *J. Org. Chem.* 2002, 67, 3643-3650.

9. Li, G. Y.; Zheng, G.; Noonan, A. F. *J. Org. Chem.* 2001, 66, 8677-8681.
10. Li, G. Y. *Angew. Chem. Int. Ed.* 2001, 40, 1513-1516.
11. Schopfer, U.; Schlapbach, A. *Tetrahedron* 2001, 57, 3069-3073.
12. Itoh, T.; Mase, T. *Organic Letters* 2004, 6, 4587-4590.
13. Kwong, F. Y.; Buchwald, S. L. *Organic Letters* 2002, 4, 3517-3520.
14. Bates, C. G.; Gujadhur, R. K.; Venkataraman, D. *Organic Letters* 2002, 4, 2803-2806.
15. Hickman, R. J. S.; Christie, B. J.; Guy, R. W.; White, T. J. *Austr. J. Chem.* 1985, 38, 899-904.
16. Palomo, C.; Oiarbide, M.; Lopez, R.; Gomez-Bengoa, E. *Tetrahedron Letters* 2000, 41, 1283-1286.
17. Wu, Y. J.; He, H. *Synlett* 2003, 1789-1790.
18. Cai, L.; Chin, F. T.; Pike, V. W.; Toyama, H.; Liow, J. S.; Zoghbi, S. S.; Modell, K.; Briard, E.; Shetty, H. U.; Sinclair, K.; Donohue, S.; Tipre, D.; Kung, M. P.; Dagostin, C.; Widdowson, D. A.; Green, M.; Gao, W.; Herman, M. M.; Ichise, M.; Innis, R. B. *J. Med. Chem.* 2004, 47, 2208-2218.
19. Wolfe, J. P.; Wagaw, S.; Marcoux, J.-F.; Buchwald, S. L. *Acc. Chem. Res* 1998, 31, 805-818.
20. Ishiyama, T.; Mori, M.; Suzuki, A.; Miyaura, N. *J. Organomet. Chem.* 1996, 525, 225-231.
21. Tang, W.; Zhang, X. *Chem. Rev.* 2003, 103, 3029-3069.

What is claimed is:

1. A compound having the formula

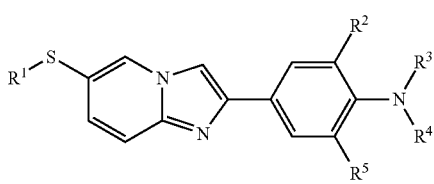

(I)

wherein:
R$^1$ is a member selected from the group consisting of C$_1$-C$_6$ alkyl and halo-substituted C$_1$-C$_6$ alkyl, or aryl alkyl;
R$^2$ is a member selected from the group consisting of H, C$_1$-C$_6$ alkyl, halo-substituted C$_1$-C$_6$ alkyl, halo, and C$_1$-C$_6$ alkylthio, and R$_3$ is a member selected from the group consisting of H and C$_1$-C$_6$ alkyl, or R$^2$ and R$^3$ are joined to form a thio-C$_1$-C$_3$ alkylene linkage or alkylene linkage, and
R$^4$ is a member selected from the group consisting of H and C$_1$-C$_3$ alkyl, and R$^5$ is a member selected from the group consisting of H and C$_1$-C$_3$ alkyl, or R$^4$ and R$^5$ are joined to form a C$_1$-C$_3$ alkylenethio linkage or alkylene linkage.

2. The compound of claim 1 wherein R$^1$ is a member selected from the group consisting of C$_1$-C$_6$ alkyl and fluoro-substituted C$_1$-C$_6$ alkyl.

3. The compound of claim 1 wherein R$^1$ is a member selected from the group consisting of C$_1$-C$_3$ alkyl and fluoro-substituted C$_1$-C$_3$ alkyl.

4. The compound of claim 1 wherein R$^1$ is a member selected from the group consisting of methyl, ethyl, fluoromethyl, and fluoroethyl.

5. The compound of claim 1 wherein R$^2$ is a member selected from the group consisting of H, C$_1$-C$_3$ alkyl, chloro, bromo, chloro-substituted C$_1$-C$_3$ alkyl, bromo-substituted C$_1$-C$_3$ alkyl, and C$_1$-C$_3$ alkylthio, and R$^3$ is a member selected from the group consisting of H and C$_1$-C$_3$ alkyl, or R$^2$ and R$^3$ are joined to form a thiomethylene or alkylene linkage.

6. The compound of claim 1 wherein R$^2$ is a member selected from the group consisting of H, bromo, and methylthio, and R$^3$ is a member selected from the group consisting of H and methyl, or R$^2$ and R$^3$ are joined to form a thiomethylene or alkylene linkage.

7. The compound of claim 1 wherein R$^4$ is a member selected from the group consisting of H and methyl, and R$^5$ is a member selected from the group consisting of H and methyl, or R$^4$ and R$^5$ are joined to form a C$_1$-C$_3$ alkylenethio or alkylene linkage.

8. The compound of claim 1 wherein R$^4$ is H and R$^5$ is H, or R$^4$ and R$^5$ are joined to form a methylenethio or alkylene linkage.

9. The compound of claim 1 wherein R$^1$ is a member selected from the group consisting of methyl, ethyl, fluoromethyl, and fluoroethyl; R$^2$ is a member selected from the group consisting of H, chloro, and methylthio, and R$^3$ is a member selected from the group consisting of H and methyl, or R$^2$ and R$^3$ are joined to form a thiomethylene or alkylene linkage; and R$^4$ is H and R$^5$ is H, or R$^4$ and R$^5$ are joined to form a methylenethio or alkylene linkage.

10. The compound of claim 1 wherein R$^1$ is a member selected from the group consisting of C$_1$-C$_6$ alkyl and fluoro-substituted C$_1$-C$_6$ alkyl; R$^2$ is a member selected from the group consisting of H, C$_1$-C$_3$ alkyl, chloro, bromo, chloro-substituted C$_1$-C$_3$ alkyl, bromo-substituted C$_1$-C$_3$ alkyl, and C$_1$-C$_3$ alkylthio, and R$^3$ is a member selected from the group consisting of H and C$_1$-C$_3$ alkyl, or R$^2$ and R$^3$ are joined to form a thiomethylene or alkylene linkage; and R$^4$ is a member selected from the group consisting of H and methyl, and R$^5$ is a member selected from the group consisting of H and methyl, or R$^4$ and R$^5$ are joined to form a C$_1$-C$_3$ alkylenethio alkylene linkage.

11. A method for imaging amyloid deposits in a patient, said method comprising administering to said patient a compound of claim 1 and imaging portions of said patient where amyloid deposits occur when said patient is suffering from Alzheimer's disease.

12. A compound of the formula

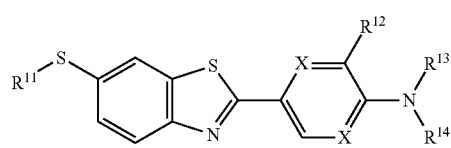

(II)

or a pharmaceutically acceptable salt thereof, wherein the compound is
(i) a compound in which R$^1$ is FCH$_2$, R$^2$ is H, R$^3$ is CH$_3$, and R$^4$ and R$^5$ are H;
(ii) a compound in which R$^1$ is FCH$_2$, R$^2$ is Br, and R$^3$, R$^4$, and R$^5$ are H;
(iii) a compound in which R$^1$ is FCH$_2$CH$_2$, R$^2$ is H, R$^3$ is CH$_3$, and R$^4$ and R$^5$ are H;
(iv) a compound in which R$^1$ is FCH$_2$CH$_2$, R$^2$ is Br, and R$^3$, R$^4$, and R$^5$ are H;
(v) a compound in which R$^1$ is FCH$_2$, R$^2$ is SCH$_3$, and R$^3$, R$^4$, and R$^5$ are H;
(vi) a compound in which R$^1$ is FCH$_2$, R$^2$ and R$^3$ are joined by SCH$_2$, and R$^4$ and R$^5$ are H; or
(vii) a compound in which R$^1$ is FCH$_2$, R$^2$ and R$^3$ are joined by SCH$_2$, and R$^4$ and R$^5$ are joined by SCH$_2$.

* * * * *

UNITED STATES PATENT AND TRADEMARK OFFICE
CERTIFICATE OF CORRECTION

| | | |
|---|---|---|
| PATENT NO. | : 8,703,096 B2 | Page 1 of 1 |
| APPLICATION NO. | : 12/293340 | |
| DATED | : April 22, 2014 | |
| INVENTOR(S) | : Lisheng Cai, Victor W. Pike and Robert B. Innis | |

It is certified that error appears in the above-identified patent and that said Letters Patent is hereby corrected as shown below:

In the Claims

Column 36, Claim 12, line 41, the structure should appear as follows:

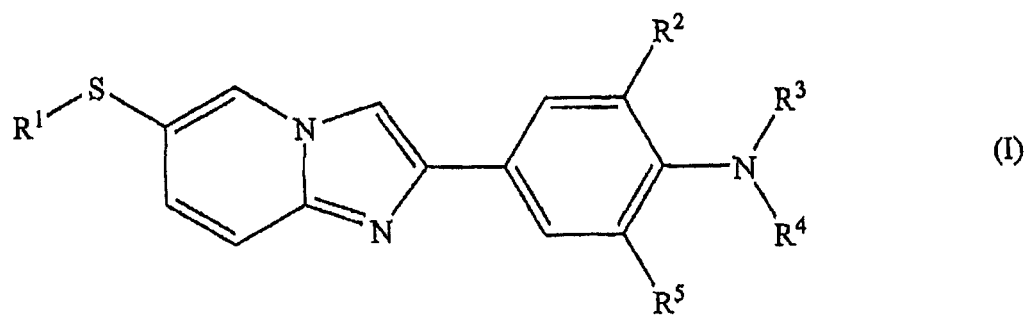

Signed and Sealed this
Tenth Day of March, 2015

Michelle K. Lee
*Deputy Director of the United States Patent and Trademark Office*